(12) United States Patent
Lubkowitz et al.

(10) Patent No.: US 8,413,484 B2
(45) Date of Patent: Apr. 9, 2013

(54) METHOD AND SYSTEM FOR CHEMICAL AND PHYSICAL CHARACTERIZATION OF COMPLEX SAMPLES

(75) Inventors: Joaquin A. Lubkowitz, Gulf Breeze, FL (US); Aaron Mendez, Gulf Breeze, FL (US); Roberto I. Meneghini, Gulf Breeze, FL (US)

(73) Assignee: Separation Systems, Inc., Gulf Breeze, FL (US)

( * ) Notice: Subject to any disclaimer, the term of this patent is extended or adjusted under 35 U.S.C. 154(b) by 180 days.

(21) Appl. No.: 11/819,861

(22) Filed: Jun. 29, 2007

(65) Prior Publication Data

US 2008/0296487 A1    Dec. 4, 2008

Related U.S. Application Data

(63) Continuation-in-part of application No. 11/582,558, filed on Oct. 18, 2006, now Pat. No. 7,509,837.

(51) Int. Cl.
  *B01D 59/44* (2006.01)
  *H01J 49/00* (2006.01)
  *G01N 30/78* (2006.01)

(52) U.S. Cl. ............ 73/23.35; 73/23.37; 73/23.39; 73/23.4; 73/23.41

(58) Field of Classification Search ............ 73/23.35, 73/23.37, 23.39, 23.4, 23.41
  See application file for complete search history.

(56) References Cited

U.S. PATENT DOCUMENTS

| | | | |
|---|---|---|---|
| 3,291,980 A | 12/1966 | Coates et al. | |
| 5,012,052 A * | 4/1991 | Hayes | 250/288 |
| 5,699,269 A | 12/1997 | Ashe et al. | |
| 5,766,954 A * | 6/1998 | Freedman et al. | 436/144 |
| 5,808,180 A | 9/1998 | Roussis et al. | |
| 6,354,136 B1 | 3/2002 | Bremer et al. | |
| 2004/0035183 A1* | 2/2004 | O'Brien et al. | 73/23.36 |
| 2005/0252275 A1* | 11/2005 | Kita et al. | 73/23.34 |
| 2006/0008491 A1* | 1/2006 | Leach et al. | 424/405 |
| 2006/0125826 A1 | 6/2006 | Lubkowitz | |

FOREIGN PATENT DOCUMENTS

| | | |
|---|---|---|
| EP | 0 833 155 A | 4/1998 |
| EP | 0 921 393 A | 6/1999 |
| WO | WO 2007/047770 A | 4/2007 |

OTHER PUBLICATIONS

Villalanti, D. C. et al., "High-Temperature Simulated Distillation Applications in Petroleum Characterization", Encyclopedia of Analytical Chemistry, 2000, pp. 6726-6741.*

Henneberg, D., "High Resolution Mass Spectra of Compounds Separated by Capillary Columns", Analytical Chemistry, vol. 38, No. 3, Mar. 1966, pp. 495-496.*

(Continued)

*Primary Examiner* — Daniel S Larkin
(74) *Attorney, Agent, or Firm* — Arent Fox LLP

(57) ABSTRACT

A method and system for rapid determination of a hydrocarbon type composition, such as crude oils and fractions thereof, and s obtaining the information necessary to assess the yield of commercially valuable fuel and lube oil fractions in a single process, variations of the method and system use Gas Chromatography-FID/Mass Spectrometry and other features, including an auto sampler, a wall coated capillary column, a temperature programmable injector, and a data processing system for compiling and processing the experimental data. The system and method further include a computer system with application software or other processing mechanism and optionally a communication network. One variation provides a graphical user interface for the entry of data and for displaying information, such as in a graphical manner, to show the relationship of various determined outputs and results.

30 Claims, 52 Drawing Sheets

OTHER PUBLICATIONS

Ohba T. et al., "Decomposition Property of Methylhydrazine with titanium Nitridationlow Temperature", Journal of the Electrochemical Society, Electrochemical Society, Manchester, New Hampsire, US, vol. 142, No. 3, Mar. 1, 1995, pp. 934-938, XP000504900.

Nitz S. Drawert F, Gellert U., "A Variable Effluent Splitter for Simultaneous Sniffing-MS-Monitoring", Chromatographia, vol. 22, No. 1-6, Jun. 1986, pp. 51-54, XP002561130, Vieweg& Sohn Verlag.

* cited by examiner

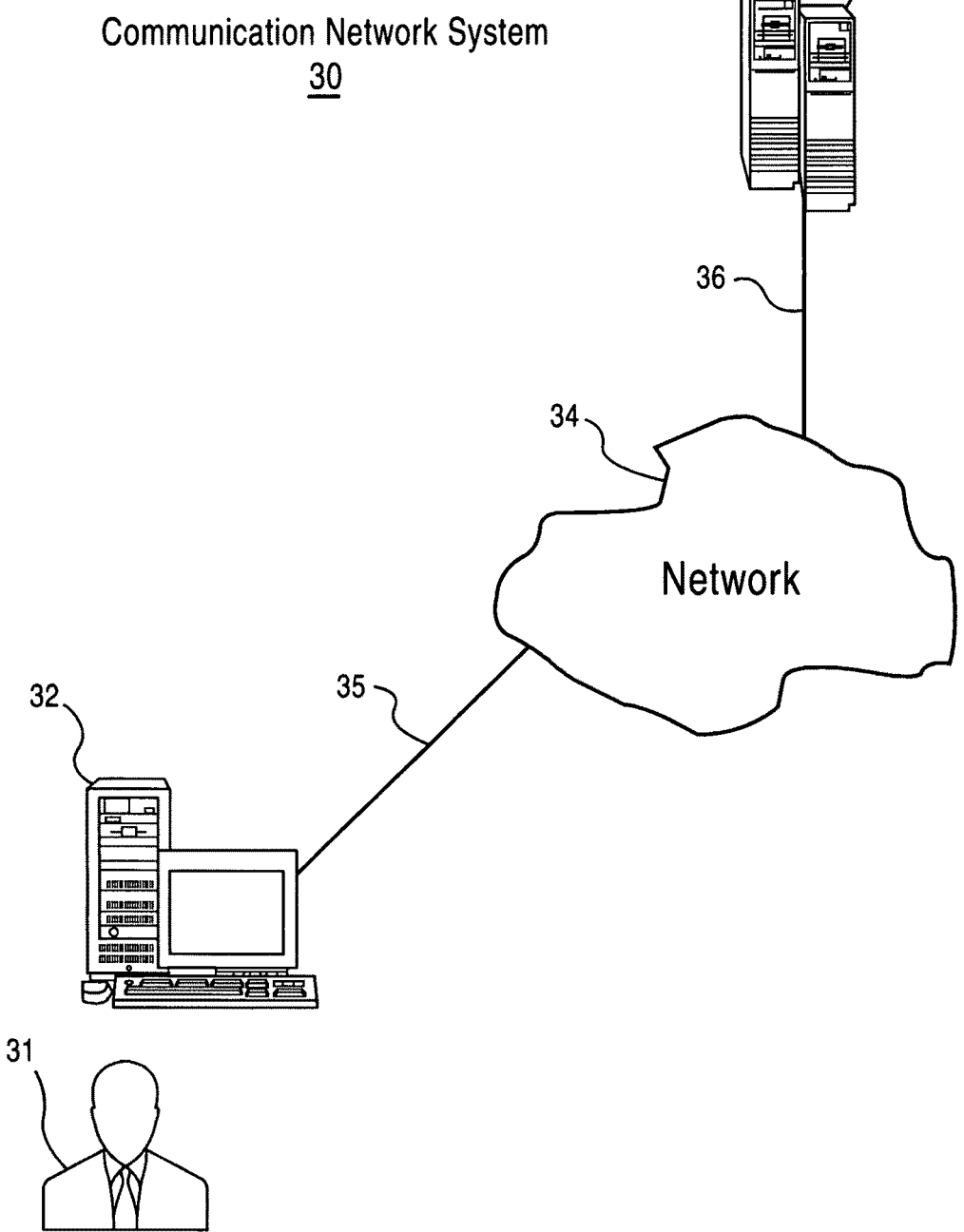

Fig. 6  Repeatability - Paraffinic Crude (3 Injections)

Fig.7  ASTM D 7169-2005 Retention Time Standard

Fig.8 Crude Oil With Boiling Point Calibration Curve

Fig.9 Reference Material 5010-A

Fig.11

*The Algorithm:*

SATURATES

Σ43 - paraffins

Σ55 - cycloparaffins

Σ81 - dicycloparaffins

Σ93 - tricycloparaffins

AROMATICS

Σ78+...91+...-mono

Σ104+...117+...-Clase II

Σ130+...129+...-Clase III

Σ128+...141+...-Clase IV

Σ154+...167+...-Clase V

Σ166+...179+...-Clase VI

Σ178+...191+...-Clase VII

Fig.12

| Compound | Class | Type | z-Series | Group |
|---|---|---|---|---|
| Alkylbenzenes | I | 0 | -6 | Monoaromatics |
| Benzothiophenes | I | 1 | -10S | Thiophenoaromatics |
| Naphthenephenantrenes | I | 2 | -20 | Triaromatics |
| Naphthenebenzenes | II | 0 | -8 | Monoaromatics |
| Pyrenes | II | 1 | -22 | Tetraaromatics |
| Unidentified | II | 2 | | Unidentified |
| Dinaphthenebenzenes | III | 0 | -10 | Monoaromatics |
| Chrysenes | III | 1 | -24 | Tetraaromatics |
| Unidenitifed | III | 2 | | Unidentified |
| Naphtalenes | IV | 0 | -12 | Diaromatics |
| Dibenzothiophenes | IV | 1 | -16S | Thiophenoaromatics |
| Unidentified | IV | 2 | | Unidentified |
| Acenaphthenes+ Dibenzofurans | V | 0 | -14-160 | Diaromatics |
| Perylenes | V | 1 | -28 | Pentaaromatics |
| Unidentified | V | 2 | | Unidentified |
| Fluorenes | VI | 0 | -16 | Diaromatics |
| Dibenzanthracenes | VI | 1 | -30 | Pentaaromatics |
| Unidentified | VI | 2 | | Unidentified |
| Phenanthrenes | VII | 0 | -18 | Triaromatics |
| Naphthobenzothiophenes | VII | 1 | -22S | Thiophenoaromatics |
| Unidentified | VII | 2 | | Unidentified |

*Group Type Analysis*

Fig. 16 *Signal Overlapping*

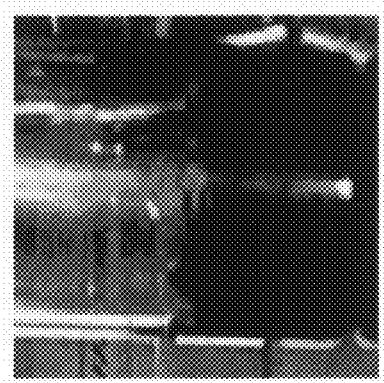
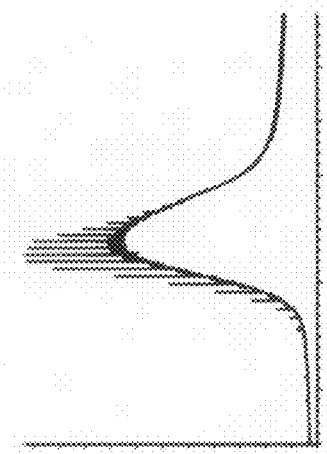
MMO
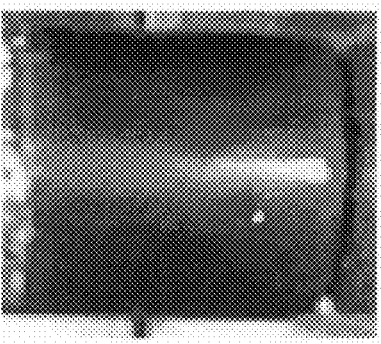
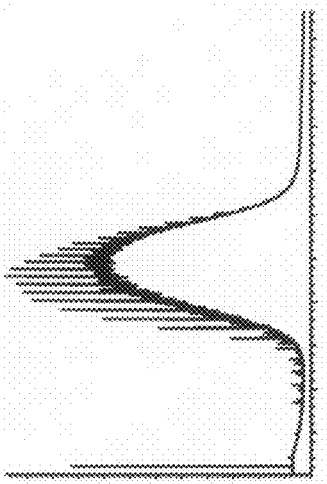
LMO
LUBE OIL FRACTIONS
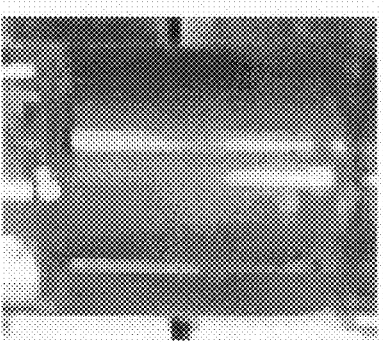
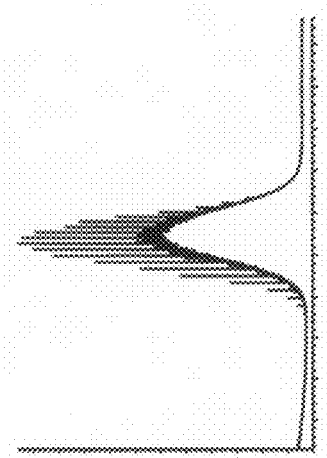
SPO
Fig. 21 ...... *Experimental Results*

Fig.22
*Hydrocarbon Type Analysis (From the Whole Crude)*

| SP | O<br>Time interval<br>21 – 33 min. | LMO<br>Time interval<br>24 – 42 min. | MMO<br>Time interval<br>28 – 56 min |
|---|---|---|---|
| - Total Saturates, %p | 76.0 (75.3) | 69.2 (69.5) | 54.2 (53.6) |
| Paraffins | 42.7 (39.7) | 33.5 (27.2) | 20.2 (17.4) |
| Monocycloparaffins | 14.3 (13.1) | 13.8 (14.2) | 12.2 (13.4) |
| Dicycloparaffins | 10.4 (7.2) | 10.9 (12.6) | 9.4 (10.3) |
| Tricycloparaffins+ | 8.6 (15.4) | 11.0 (15.4) | 12.3 (12.6) |
| - Total Aromatics, %p | 24.0 (24.7) | 30.8 (30.5) | 45.8 (46.4) |
| Monoaromatics | 10.8 (10.5) | 11.9 (12.9) | 20.7 (21.0) |
| Benzenes | 3.8 (3.3) | 3.8 (4.0) | 7.1 (7.0) |
| Naphthenebenzenes | 3.2 (3.4) | 3.7 (4.0) | 6.3 (6.5) |
| Dinaphthenebenzenes | 3.9 (3.7) | 4.4 (4.9) | 7.2 (7.4) |
| - Diaromatics | 4.0 (5.2) | 5.4 (3.5) | 7.6 (6.9) |
| Naphthalenes | 0.0 (0.0) | 0.0 (0.0) | 0.0 (0.0) |
| Acenaphthenes, Dibenzofurans | 1.4 (2.5) | 1.9 (0.8) | 1.8 (2.0) |
| Fluorenes | 2.6 (2.7) | 3.5 (2.7) | 5.7 (4.9) |
| - Triaromatics | 2.7 (1.9) | 3.8 (2.2) | 1.7 (3.0) |
| Phenanthrenes | 2.0 (1.1) | 2.4 (1.0) | 1.2 (1.6) |
| Naphthenophenanthrenes | 0.7 (0.9) | 1.4 (1.2) | 0.6 (1.4) |
| - Tetraaromatics | 1.7 (2.1) | 3.1 (4.3) | 4.7 (3.4) |
| Pyrenes | 1.4 (1.60 | 2.2 (2.7) | 2.7 (1.8) |
| Chrysenes | 0.3 (0.5) | 1.0 (1.6) | 1.9 (1.6) |
| - Pentaaromatics | 0.0 (0.6) | 0.3 (0.5) | 0.8 (1.3) |
| Perylenes | 0.0 (0.6) | 0.2 (0.4) | 0.5 (1.1) |
| Dibenzanthracenes | 0.0 (0.0) | 0.1 (0.1) | 0.3 (0.2) |
| - Thiophenes | 4.7 (4.2) | 6.2 (6.8) | 7.3 (6.8) |
| Benzothiophenes | 2.4 (2.1) | 2.5 (2.3) | 2.6 (2.4) |
| Dibenzothiophenes | 2.1 (2.1) | 3.2 (2.9) | 3.6 (3.2) |
| Naphthobenzothiophenes | 0.2 (0.0) | 0.5 (1.6) | 1.1 (1.2) |
| Unidentified Aromatics | 0.0 (0.0) | 0.1 (0.3) | 3.1 (4.1) |
| Class II | 0.0 (0.0) | 0.1 (0.0) | 0.3 (1.1) |
| Class III | 0.0 (0.0) | 0.0 (0.0) | 0.3 (0.4) |
| Class IV | 0.0 (0.0) | 0.0 (0.3) | 2.3 (2.2) |
| Class V | 0.0 (0.0) | 0.0 (0.0) | 0.0 (0.0) |

Fig.23

| | SPO Time interval 21-33 mins. | MMO Time interval 24-42 min. | LMO Time interval 28-56 mins. |
|---|---|---|---|
| *Hydrocarbon Type Analysis (From the Whole Crude)* | | | |
| Unidentified Aromatics | 0.0 (0.0) | 0.1 (0.3) | 3.1 (4.1) |
| Class II | 0.0 (0.0) | 0.1 (0.0) | 0.3 (1.1) |
| Class III | 0.0 (0.0) | 0.0 (0.0) | 0.3 (0.4) |
| Class IV | 0.0 (0.0) | 0.0 (0.3) | 2.3 (2.2) |
| Class V | 0.0 (0.0) | 0.0 (0.0) | 0.0 (0.0) |
| Class VI | 0.0 (0.0) | 0.0 (0.0) | 0.0 (0.1) |
| Class VII | 0.0 (0.0) | 0.0 (0.0) | 0.1 (0.3) |

Fig.24

COMPARATIVE STUDY OF MIDDLE HYDROCARBON SAMPLES

| SAMPLE | TOTAL AROMATICS CONTENT %w | | | |
|---|---|---|---|---|
| | SFC ASTM D 5186 | | MS Group Type | |
| | Mono | | Mono | |
| Low Sulphur Diesel | 23.8 | | 27.27 | |
| Jet Fuel | 14.57 | | 12.19 | |
| Light Catalytic Gas Oil | 30.51 | | 33.74 | |

*- Poliolefins matrix interference

Fig.27
Quantitative Analysis for groups

AROMATIC

78+..91+... - mono

104+...117+... -Clase II

130+...129+... - Clase III

128+...141+... -Clase IV

154+...167+... -Clase V

166+...179+... -Clase VI

178+...191+... -Clase VII

SATURATED

43 - paraffins

55 - cycloparaffins

81 - dicycloparaffins

93 - tricycloparaffins

C.J. Robinson. Analytical Chemistry, vol. 43, 11, 1971

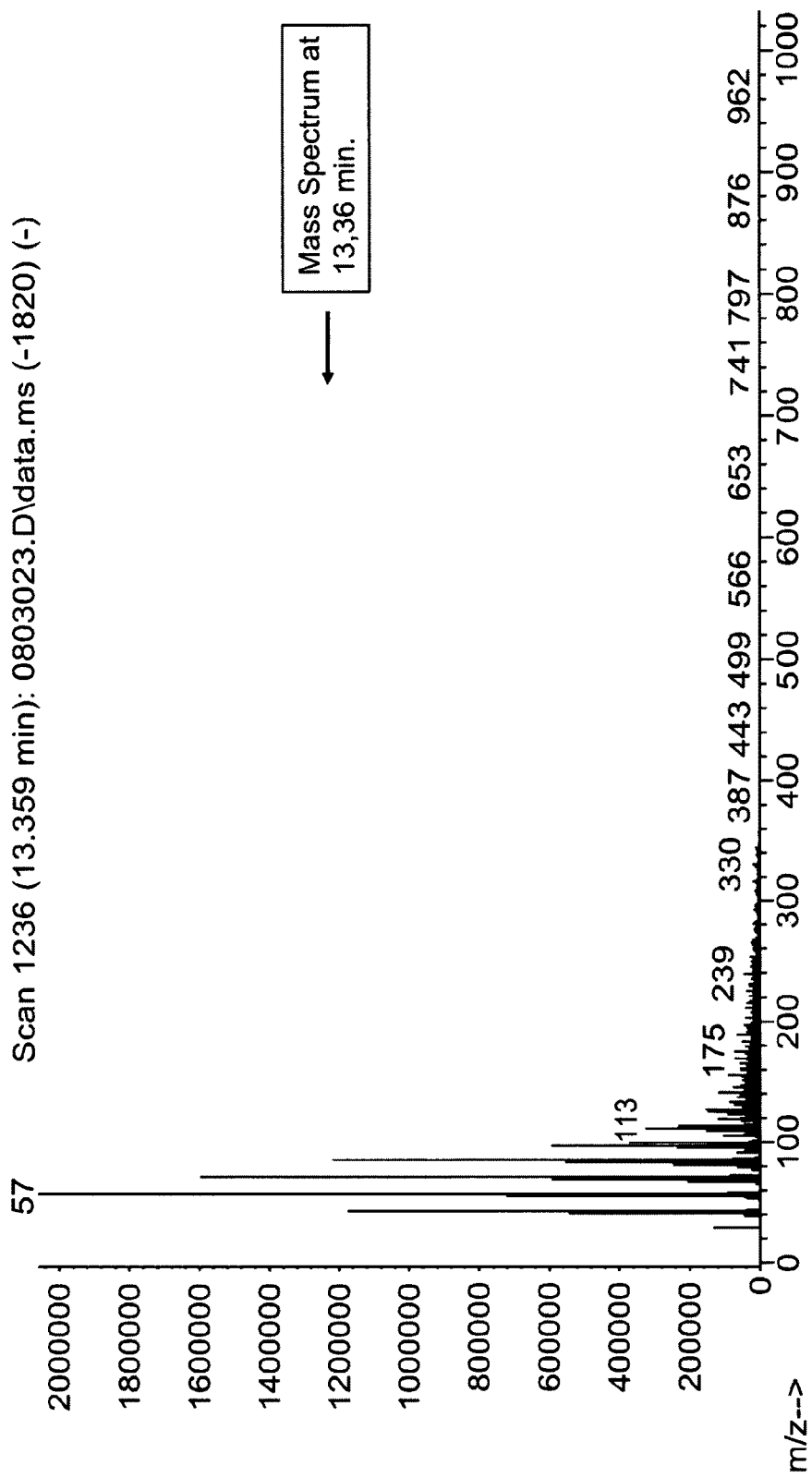
Fig. 29 SIM DIS FID / MS Analysis

Fig.30

| | | Typical Report |
|---|---|---|
| - Total Ariomatics %p | 24.0 (24.7) | |
| Monoaromatics | 10.8 (10.5) | |
| benzenes | 3.8 (3.3) | |
| naphthenebenzenes | 3.2 (3.4) | |
| Dinaphthenebenzenes | 3.9 (3.7) | |
| Diaromatics | 4.0 (5.2) | |
| Naphthalenes | 0.0 (0.0) | |
| Acenaohthenes, Dibenzothiophenes | 1.4 (2.5) | |
| Fluorenes | 2.6 (2.7) | |
| Triaromatics | 2.7 (1.9) | |
| Phenanthrenes | 2.0 (1.1) | |
| naphthenephenantrenes | 0.7 (0.9) | |
| tetraaromatics | 1.7 (2.1) | |
| pyrenes | 1.4 (1.60) | |
| chrysenes | 0.3 (0.5) | |
| pentaaromatics | 0.0 (0.6) | |
| preylenes | 0.0 (0.6) | |
| dibenzofurans | 0.0 (0.0) | |
| -thiophenoaromatics | 4.7 (4.2) | |
| benzothiophenes | 2.4 (2.1) | |
| dibenzothiophenes | 2.1 (2.1) | |
| naphthobenzothioph | 0.2 (0.0) | |
| Unidentified Aromatics | 0.0 (0.0) | |

| -Total Saturated %p | 76.0 (75.3) |
|---|---|
| Paraffins | 42.7 (39.7) |
| Monoparaffins | 14.3 (13.1) |
| dicycloparaffins | 10.4 (7.2) |
| Tricycloparaffins+ | 8.6 (15.4) |

Fig.31

COMPARATIVE STUDY OF MEDIUM DISTILLATIONS

Total Aromatics %w

|  | Mono | Total | Mono | Total |
|---|---|---|---|---|
| Diesel | 23.18 | 33.23 | 27.27 | 36.64 |
| Jet Fuel | 14.57 | 18.38 | 12.19 | 16.90 |
| Gas Oil | 30.51 | 75.25 | 33.74 | 87.26* |

Fig. 36

Medium Crude                                                                 Repeatability (3 Injections)

Boiling Point Table (%Off)

| %Off | BP(F) | BP(F) | BP(F) | Avg | %SDV |
|---|---|---|---|---|---|
| IBP | 260.1 | 260.1 | 260.1 | 260.1 | 0.0 |
| 5.00 | 354.9 | 354.7 | 355.5 | 355.0 | 0.1 |
| 10.00 | 453.9 | 453.5 | 454.6 | 454.0 | 0.1 |
| 15.00 | 532.8 | 532.3 | 534.0 | 533.1 | 0.2 |
| 20.00 | 604.7 | 604.4 | 605.6 | 604.9 | 0.1 |
| 25.00 | 677.8 | 677.4 | 679.3 | 678.2 | 0.1 |
| 30.00 | 751.0 | 750.7 | 752.5 | 751.4 | 0.1 |
| 35.00 | 818.4 | 818.2 | 819.8 | 818.8 | 0.1 |
| 40.00 | 886.6 | 886.3 | 888.2 | 887.0 | 0.1 |
| 45.00 | 957.6 | 957.2 | 959.4 | 958.1 | 0.1 |
| 50.00 | 1033.8 | 1033.3 | 1035.7 | 1034.3 | 0.1 |
| 55.00 | 1107.7 | 1107.3 | 1109.7 | 1108.3 | 0.1 |
| 60.00 | 1175.0 | 1174.8 | 1176.8 | 1175.5 | 0.1 |
| 65.00 | 1232.3 | 1231.1 | 1232.8 | 1232.0 | 0.1 |
| 70.00 | 1297.0 | 1294.2 | 1295.0 | 1295.4 | 0.1 |

Boiling Point Table

| File | Sample Id | Start Time | End Time | %Recovery | %Recovery Used |
|---|---|---|---|---|---|
| C:\msdchem\1\DATA\MEXICO\05230608.D\05230608_FID.cdf | CrudoMedianoI | | | 72.28 | 72.28 |
| C:\msdchem\1\DATA\MEXICO\05230609.D\05230609_FID.cdf | CrudoMedianoII | | | 72.61 | 72.61 |
| C:\msdchem\1\DATA\MEXICO\05230610.D\05230610_FID.cdf | CrudoMedianoIII | | | 72.59 | 72.59 |

Fig. 38

*Heavy Crude*

Boiling Point Table (%Off)

| %Off | BP(F) |
|---|---|
| IBP | 175.1 |
| 5.00 | 362.9 |
| 10.00 | 495.6 |
| 15.00 | 598.6 |
| 20.00 | 688.6 |
| 25.00 | 773.8 |
| 30.00 | 848.4 |
| 35.00 | 922.8 |
| 40.00 | 997.3 |
| 45.00 | 1070.9 |
| 50.00 | 1135.5 |
| 55.00 | 1185.9 |
| 60.00 | 1226.6 |
| 65.00 | 1273.9 |
| 70.00 | 1319.8 |

Boiling Point Table

%Recovery       70.81 @ 1328.0F
%Recovery Used  70.81
File            C:\msdchem\1\DATA\MEXICO\05230615.D\05230615_FID.cdf
Sample Id       Crudo Pesado1
LIMS Id
Parameter File  SIMDISMFCRYO

Fig. 40

Integrated Product

Boiling Point Table (%Off)

Boiling Point Table

| %Off | BP(F) |
|---|---|
| IBP | 259.1 |
| 5.00 | 489.4 |
| 10.00 | 609.9 |
| 15.00 | 686.8 |
| 20.00 | 745.3 |
| 25.00 | 794.0 |
| 30.00 | 840.4 |
| 35.00 | 885.5 |
| 40.00 | 933.0 |
| 45.00 | 982.5 |
| 50.00 | 1036.3 |
| 55.00 | 1091.6 |
| 60.00 | 1151.9 |
| 65.00 | 1208.8 |
| 70.00 | 1271.0 |

%Recovery         74.57 @ 1328.0F
%Recovery Used   74.57
File              C:\msdchem1\DATA\MEXICO\05230604.D\05230604_FID.cdf
Sample Id         Producto Integrado
LIMS Id
Parameter File    SIMDISMFCRYO

Fig.41

Fraction Yield

| Fraction | Yield % | | |
| --- | --- | --- | --- |
| | Medium Crude | Heavy Crude | Integrated Product |
| Medium Distillation 420°F – 755°F | 22.05 | 16.91 | 17.77 |
| Lubricants 650°F – 1000°F | 24.84 | 22.30 | 34.28 |

Fig. 43

| %Off | BP(F) |
|------|-------|
| IBP | 259.8 |
| 5.00 | 348.4 |
| 10.00 | 444.7 |
| 15.00 | 521.5 |
| 20.00 | 598.2 |
| 25.00 | 665.9 |
| 30.00 | 736.9 |
| 35.00 | 804.1 |
| 40.00 | 871.1 |
| 45.00 | 939.8 |
| 50.00 | 1012.6 |
| 55.00 | 1086.8 |
| 60.00 | 1156.7 |
| 65.00 | 1211.9 |
| 70.00 | 1273.8 |

Boiling Point Table

%Recovery       74.38 @ 1328.0F
%Recovery Used  74.38
File            C:\msdchem\1\DATA\MEXICO\05230612.D\05230612_FID.cdf
Sample Id       Crudo Maya
LIMS Id
Parameter File  SIMDISMFCRYO

CRUDE MAY

Fig. 45

Boiling Point Table (%Off) — RX 24 F.L.

| %Off | BP(F) |
|---|---|
| IBP | 265.0 |
| 5.00 | 376.3 |
| 10.00 | 391.4 |
| 15.00 | 393.5 |
| 20.00 | 396.7 |
| 25.00 | 489.6 |
| 30.00 | 578.2 |
| 35.00 | 662.8 |
| 40.00 | 747.3 |
| 45.00 | 826.2 |
| 50.00 | 906.7 |
| 55.00 | 991.9 |
| 60.00 | 1080.5 |
| 65.00 | 1162.8 |
| 70.00 | 1228.6 |
| 75.00 | 1302.6 |

Boiling Point Table

%Recovery       76.61 @ 1328.0F
%Recovery Used  76.61
File            C:\msdchem1\1DATA\MEXICO\05230614.D\05230614_FID.cdf
Sample Id       RX 24
LIMS Id
Parameter File  SIMDISMFCRYO

METHOD AND SYSTEM FOR CHEMICAL AND PHYSICAL CHARACTERIZATION OF COMPLEX SAMPLES This application is a Continuation-In-Part Application of and claims priority to U.S. patent application Ser. No. 11/582,558, filed Oct. 18, 2006 now U.S. Pat. No. 7,509,837, and entitled METHODS AND SYSTEMS FOR CHEMICAL AND PHYSICAL CHARACTERIZATION OF COMPLEX SAMPLES. The entire content of this application is incorporated herein by reference.

BACKGROUND OF THE INVENTION

1. Field of the Invention

The present invention relates to a method and system for rapid determination of composition, of crude oils and fractions thereof, as well as other substances and obtaining the information necessary to assess the yield of commercially valuable fuel and lube oil fractions, for example, in a single process. In particular, the present invention is directed to a method and system for determining yields and compositions in terms of a simultaneous boiling point distributions and hydrocarbon types breakdown, across the boiling range of interest, and determining the changes in chemical composition and yields in upgrading and/or conversion processes, compiling a preliminary evaluation of a variety of geochemical parameters or biomarkers for the correlation to fingerprint identification, maturity, origins, etc., and compiling experimental data to chemical and physical properties.

2. Background of the Technology

Gas Chromatography is a chemical analysis instrument for separating chemicals in a complex sample. A gas chromatograph uses a narrow tube, known as a column, through which different chemical constituents of a sample pass in a gas stream. The gas stream is also called the carrier gas or mobile phase. Gas Liquid Chromatography (GLC), or simply Gas Chromatography (GC) is a type of chromatography in which the mobile phase is a gas. The chemical constituents within the sample pass through the column at different rates, depending on their various chemical and physical properties and their interaction with a specific column phase. This column phase is called the stationary phase and is a microscopic layer of liquid on an inert solid support in the column. If the phase is bonded directly to the tubing it is called a capillary column The column is often flexible so that a very long column can be wound into a small coil.

The column(s) in a GC are contained in an oven, the temperature of which is precisely controlled (e.g., electronically). The rate at which a sample passes through the column is directly proportional to the temperature of the column. The higher the column temperature, the faster the sample moves through the column. However, when a sample moves quickly through the column, it interacts less with the stationary phase, and the analytes are less separated.

As the chemical constituents exit the end of the column, they are detected and identified electronically by a detector. The stationary phase separates the different components, causing each one to exit the column at a different time, which is called the retention time. Other parameters can also be used to alter the order or time of the retention, such as the carrier gas flow rate and the temperature as well as the chemical nature of the phase.

However, conventional GC may require high resolution techniques in order to provide a satisfactory analysis of the chemical constituents of a complex sample.

SUMMARY OF THE INVENTION

There is a need in the art, therefore, for methods and systems for analyzing complex samples using gas chromatography that do not require high resolution techniques. The present invention solves the above-identified needs, as well as others by providing methods and systems for rapid determination of composition of crude oils and fractions thereof, as well as other substances, and in a single process obtaining the information necessary to assess the yield of commercially valuable petroleum fuel and lube oil fractions using Gas Chromatography-FID/Mass Spectrometry. Variations of the present invention also include auto sampler features, a wall coated capillary column, a temperature programmable injector and data processing features for compiling and processing experimental data. Embodiments of the present invention further include a computer system with application software and a communication network. The present invention, in one embodiment, provides a graphical user interface for the entry of data, and for displaying information, such as in a graphical manner, to show the relationship of various determined outputs and results.

Among other things, the present invention enables multi-dimensionality with simple hardware, wherein a low resolution column is sufficient for analyses and additional highly resolving techniques are not required. In addition, the present invention provides hydrocarbon type analysis and Simulated Distillation ("SimDis") data, including providing such analysis and data in a single process.

Additional advantages and novel features of the invention will be set forth in part in the description that follows, and in part will become more apparent to those skilled in the art upon examination of the following or upon learning by practice of the invention.

BRIEF DESCRIPTION OF THE FIGURES

For a more complete understanding of the present invention, the needs satisfied thereby, and the objects, features, and advantages thereof, reference is now made to the following description taken in connection with the accompanying drawings.

FIG. 3 shows an exemplary communication system of the present invention for use with the computer system 1 of FIG. 2.

FIG. 11 shows algorithms for aromatics and saturates.

FIG. 12 shows a group type analysis of compounds that may be found within crude oil.

FIG. 21 shows the results for samples of lube oil fractions, as analyzed according to a method and system of an embodiment of the present invention.

FIG. 22 shows a hydrocarbon type analysis from a whole crude sample, as analyzed according to a method and system of an embodiment of the present invention.

FIG. 23 shows a hydrocarbon type analysis from a whole crude sample, produced in accordance with a method and system of an embodiment of the present invention.

FIG. 24 shows a comparative study of middle hydrocarbon samples, as analyzed according to a method and system of an embodiment of the present invention.

FIGS. 25-51 contain various data and other information produced using systems and methods of the present invention.

DETAILED DESCRIPTION

Figure 1:
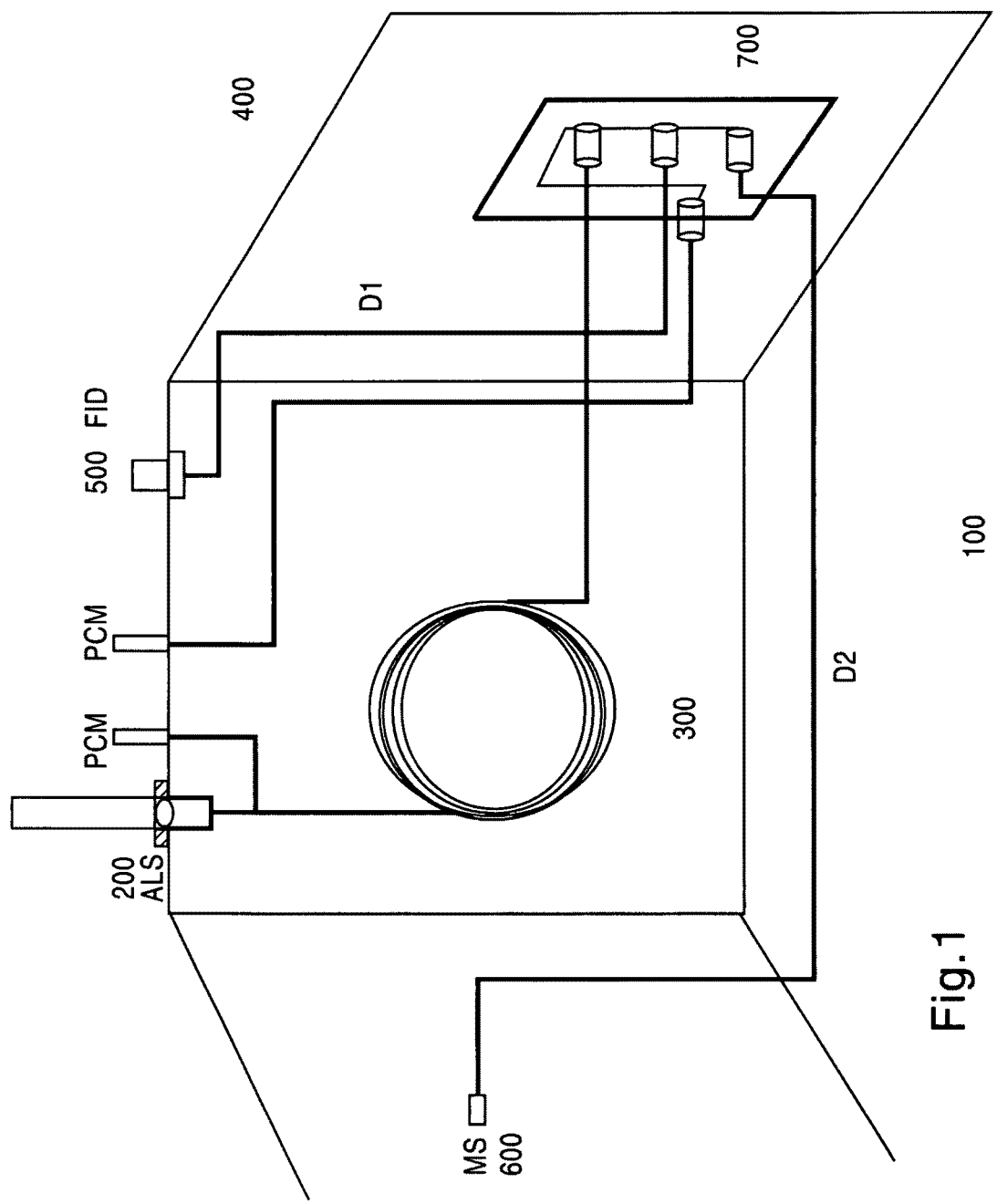
FIG. 1 shows a diagram of an exemplary Gas Chromatography-FID/Mass Spectrometry apparatus (GC-FID/MS) according to an embodiment of the present invention.

Referring now to FIG. 1, therein shown is the general architecture of an exemplary Gas Chromatography-FID/Mass Spectrometry apparatus (GC-FID/MS), as used in accordance with a method and system of the present invention.

The GC-FID/MS of FIG. 1 includes a gas chromatograph (100), which includes an injector (200), a column (300), and an oven (400); a mass spectrometer (MS) (600); a flame ion detector (FID) (500); a divider (700); and a data processing system for acquiring and processing the data. One variation provides a graphical user interface for the entry of data and for displaying information, such as in a graphical manner, to show the relationship of various determined outputs and results.

In certain embodiments, the GC-FID/MS may also include an automatic liquid sampler (ALS). In addition, the column may be a wall coated capillary column, and the inlet may be a temperature programmable injector.

In operation, the gas chromatograph (100) utilizes the difference in chemical properties between different chemical constituents in a sample to separate the chemical constituents. As the different chemical constituents exit the gas chromatograph at different times, the mass spectrometer, which is located downstream in the gas flow, evaluates the chemical constituents separately and is able to identify the constituents.

The mass spectrometer (600) identifies the various chemical constituents that pass through it at a flow D2 by breaking each constituent into ionized fragments and detecting these fragments using the mass to charge ratio of the fragments.

The FID (500) is, for example, an ion detector that uses an air-hydrogen flame to produce ions. As the chemical constituents in the sample exit the gas chromatograph at a flow D1, they pass through the flame and are burned, producing ions. The ions then produce an electric current, which is used to provide the signal output of the FID. The FID of some embodiments can only detect components that can be burned, and the FID destroys the components during detection. Thus, no further detection is made after the FID completes processing.

However, it should be noted that the nature and amount of constituents that flow through the mass spectrometer 600 and through the FID 500 may be similar in order to combine the results obtained by the MS 600 and by the FID 500. For this reason, the apparatus of this embodiment of the present invention also includes a divider (700) that divides the exiting chemical constituent between the FID and the MS, so that portions of the exiting chemical constituent are analyzable by both the FID and MS simultaneously. The divider 700 should be able to prevent molecule discrimination in the constituents and distribute the constituents equally between the flow D1 and the flow D2, which is achieved by heating the constituents at a temperature necessary to ensure that no molecular discrimination occurs. Furthermore, pneumatic control module (PCM) may be part of the GC-FID/MS, that controls the pressure of the sample as it passes through the divider in order to preserve an equal ratio of constituents flowing through D1, and another PCM that controls the pressure of the sample as it passes through the divider in order to preserve an equal ratio of constituents flowing through D2, so that the amount of constituents that pass through D1 is about equal to the amount of constituents that pass through D2. In one embodiment, the divider may be or include a micro influx divider. In one embodiment, the division between the portion of the exiting chemical constituent that is sent to the MS (D2) and the portion of the exiting chemical constituent that is sent to the FID (D1) are approximately equal, so that approximately D2/D1=1. The influx of chemical constituents are precisely divided in a controlled manner without compromising the sample integrity. The controlled division of the elution of the column towards the two detectors is prevented from being discriminatory, either of light components or of heavy components, for the samples under analysis.

An exemplary embodiment, of the present invention uses a megabore capillary high throughput column and a temperature programmable injector. In one embodiment, the column includes a capillary column element that is about 5 m by 0.53 mm i.d. by about 0.1 µm; the FID detector is an FID 440 Celsius; the carrier gas is Helium at a constant flux rate of about 12 mL/min; the oven is programmed to start at about 40° Celsius, to raise about 10° Celsius/min until about 430° Celsius is reached, to maintain the temperature for about 12 minutes, with an equilibrium time of about two minutes; the injection volume is about 0.2 µL; and the dilution is about 2% in CS2. It should be noted that hydrogen could be used instead of helium as the carrier gas.

In one embodiment of the present invention, the GC-FID/MS may be used to analyze the physical and chemical characterization of petroleum fractions. Using the GC-FID/MS, a rapid determination may be made of the composition of crude oils, for example. This apparatus and method may also be applied to fractions of crude oil, or other substance. Information necessary to access the yield of commercially available valuable fuel and lube oil fractions can also be obtained in a single process. Using quantitative software or other processing, the mass spectral data may be converted to weight and volume percent chemical composition. The system and method provide the boiling point distribution and chemical composition of the analyzed substance based on saturate and aromatic group types.

Crude oil, for example, may contain a mixture of chemical compounds from a family of several hundred chemical compounds. Some chemicals that may be found in crude oil include hexane, jet fuels fraction, diesel fractions, benzene, toluene, xylenes, naphthalene, in addition to other petroleum products such as heavy diesel, atmospheric residues, vacuum residues and naphtha to be used in gasolines. The characterization of complex fractions and versatility are improved by combining the signals of the FID detector and the mass spectrometer detector in a single processing apparatus. In an exemplary embodiment, the signal from the FID detector is in the simulated distillation mode and the MD detector is in a single environment of synergistic mode. The MD detector provides ion fragmentation at continuous time intervals during the elution of the sample though the column.

The present invention thus is able to provide a powerful analytical tool allowing the simultaneous physical and chemical characterization of whole crude oil samples and their fractions, without the need to perform the physical separation of the hydrocarbon fractions.

In an exemplary embodiment, the FID detector is in a simulated distillation mode. Simulated distillation (SimDis) is a gas chromatography technique that separates individual hydrocarbon components in their order of boiling points and is used to simulate the time-consuming laboratory-scale physical distillation procedure referred to as true boiling point distillation. Using a gas chromatograph equipped with an oven and inlet that can be temperature programmed, an FID is used for detection and measurement of the hydrocarbon analytes. The result of SimDis analysis provides a distillation curve which is a quantitative percent mass yield as a function of boiling point of the hydrocarbon components of the sample.

In some embodiments, the present invention conforms with the ASTM (American Society for Testing and Materials) standards for stimulated distillation: D-2887, D-6352, and D-7169. Simulated distillation is a proven and accepted technique for the physiochemical characterization of crude and fractions of oil. Recently, ASTM D2 accepted a new method for the analysis of fractions with a final boiling point of 615 Celsius (C5 to C60). See ASTM D 7213-05.

The quantitative methods of mass spectrometry can also serve as helpful tools in the chemical characterization of products with a vast range of boiling points. Mass spectrometry reports a composition in the basis of five principal groups: paraffin, napthalene, aromatic, sulfur, and non-identified. All of the ASTM methods, with the exception of those applying to napthalenes, require a chromatographic separation of the saturated and aromatics. Such separation requires high resolution methods. High resolution requires complex and costly equipment. New multidimensional analytical mechanisms, such as GC×GC and GC-MS-TOF, also require complex instruments and procedures, even for the gasoline range.

The present invention enables spectrometric analysis within fractions at a low resolution. Thus, it allows simple and quick analysis.

Figure 2:
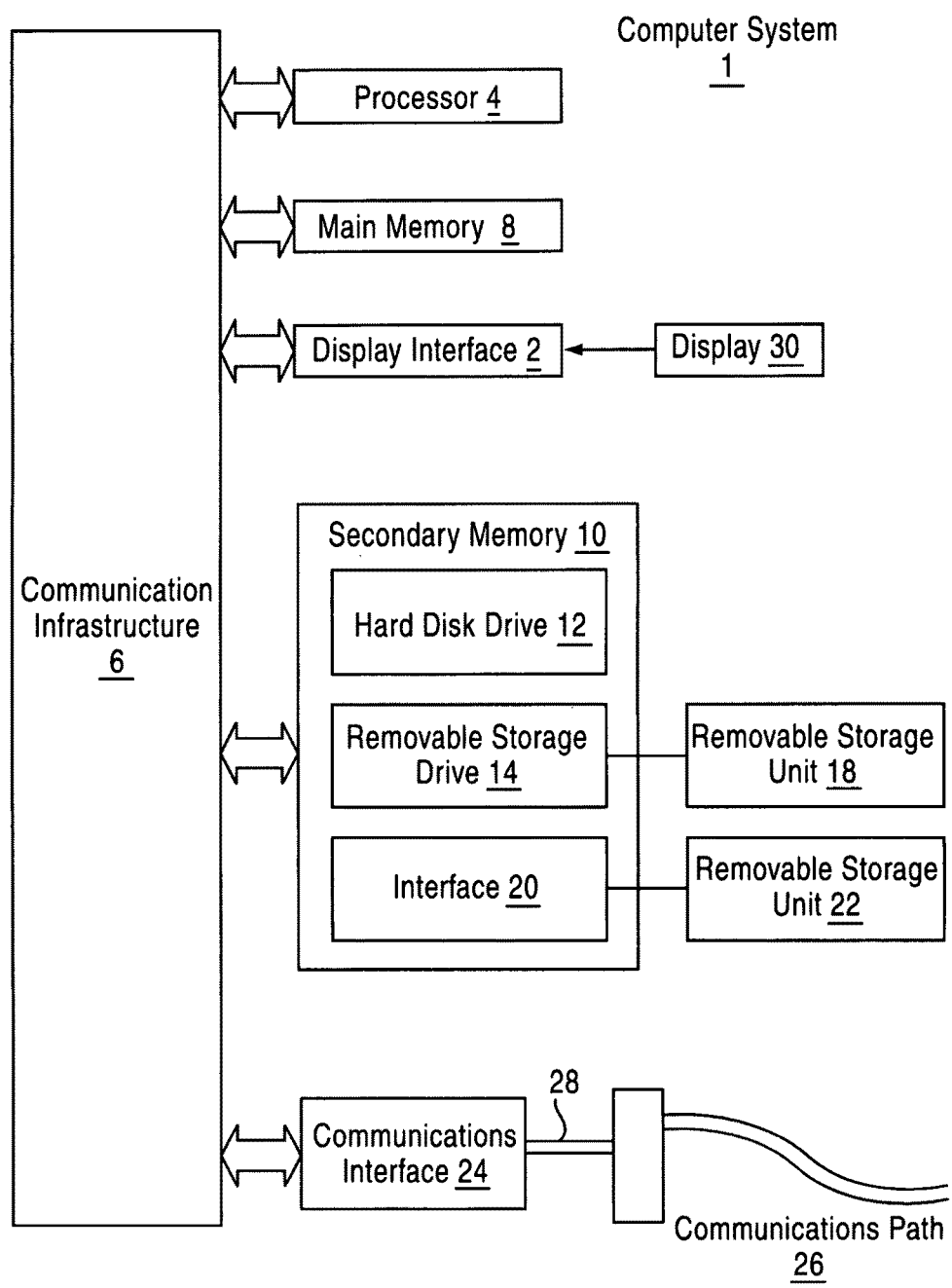
FIG. 2 illustrates a block diagram of various exemplary computer system components for use in accordance with one embodiment of the present invention

FIG. 2 illustrates a block diagram of various computer system components useable with an exemplary implementation of a physical and chemical characterization of petroleum fractions by GC/SIMDIS/MS, in accordance with embodiments of the present invention.

As shown in FIG. 2, the controller of the present invention may be implemented using hardware, software or a combination thereof and may be implemented in one or more computer systems or other processing systems. In one embodiment, the invention is directed toward one or more computer systems capable of carrying out the functionality described herein.

FIG. 2 shows a computer system 1 that includes one or more processors, such as processor 4. The processor 4 is connected to a communication infrastructure 6 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 1 can include a display interface 2 that forwards graphics, text, and other data from the communication infrastructure 6 (or from a frame buffer not shown) for display on the display unit 30. Computer system 1 also includes a main memory 8, preferably random access memory (RAM), and may also include a secondary memory 10. The secondary memory 10 may include, for example, a hard disk drive 12 and/or a removable storage drive 14, representing a floppy disk drive, a magnetic tape drive, an optical disk drive, etc. The removable storage drive 14 reads from and/or writes to a removable storage unit 18 in a well known manner. Removable storage unit 18, represents a floppy disk, magnetic tape, optical disk, etc., which is read by and written to removable storage drive 14. As will be appreciated, the removable storage unit 18 includes a computer usable storage medium having stored therein computer software and/or data.

In alternative embodiments, secondary memory 10 may include other similar devices for allowing computer programs or other instructions to be loaded into computer system 1. Such devices may include, for example, a removable storage unit 22 and an interface 20. Examples of such may include a program cartridge and cartridge interface (such as that found in video game devices), a removable memory chip (such as an erasable programmable read only memory (EPROM), or programmable read only memory (PROM)) and associated socket, and other removable storage units 22 and interfaces 20, which allow software and data to be transferred from the removable storage unit 22 to computer system 1.

Computer system 1 may also include a communications interface 24. Communications interface 24 allows software and data to be transferred between computer system 1 and external devices. Examples of communications interface 24 may include a modem, a network interface (such as an Ethernet card), a communications port, a Personal Computer Memory Card International Association (PCMCIA) slot and card, etc. Software and data transferred via communications interface 24 are in the form of signals 28, which may be electronic, electromagnetic, optical or other signals capable of being received by communications interface 24. These signals 28 are provided to communications interface 24 via a communications path (e.g., channel) 26. This path 26 carries signals 28 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 14, a hard disk installed in hard disk drive 12, and signals 28. These computer program products provide software to the computer system 1. The invention is directed to such computer program products.

Computer programs (also referred to as computer control logic) are stored in main memory 8 and/or secondary memory 10. Computer programs may also be received via communications interface 24. Such computer programs, when executed, enable the computer system 1 to perform the features of the present invention, as discussed herein. In particular, the computer programs, when executed, enable the processor 4 to perform the features of the present invention. Accordingly, such computer programs represent controllers of the computer system 1.

In an embodiment where the invention is implemented using software, the software may be stored in a computer program product and loaded into computer system 1 using removable storage drive 14, hard drive 12, or communications interface 24. The control logic (software), when executed by the processor 4, causes the processor 4 to perform the functions of the invention as described herein. In another embodiment, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

FIG. 3 shows a communication system 30 of the present invention for use with the computer system 1 of FIG. 2. The communication system 30 includes an accessor 31 (also referred to interchangeably herein as a "user") and a terminal 32. In one embodiment, data for use in the computer system 1 is, for example, input and/or accessed by the accessor 31 via the terminal 32, such as a personal computer (PC), minicomputer, mainframe computer, microcomputer, telephonic device, or wireless device, such as a hand-held wireless device coupled to a server 33, such as a PC, minicomputer, mainframe computer, microcomputer, or other device having a processor and a repository for data and/or connection to a processor and/or repository for data, via, for example, a network 34, such as the Internet or an intranet, and couplings 35, 36. The couplings 35, 36 include, for example, wired, wireless, or fiberoptic links. In another embodiment, the method and system of the present invention operate in a stand-alone environment, such as on a single terminal.

Figure 3B:
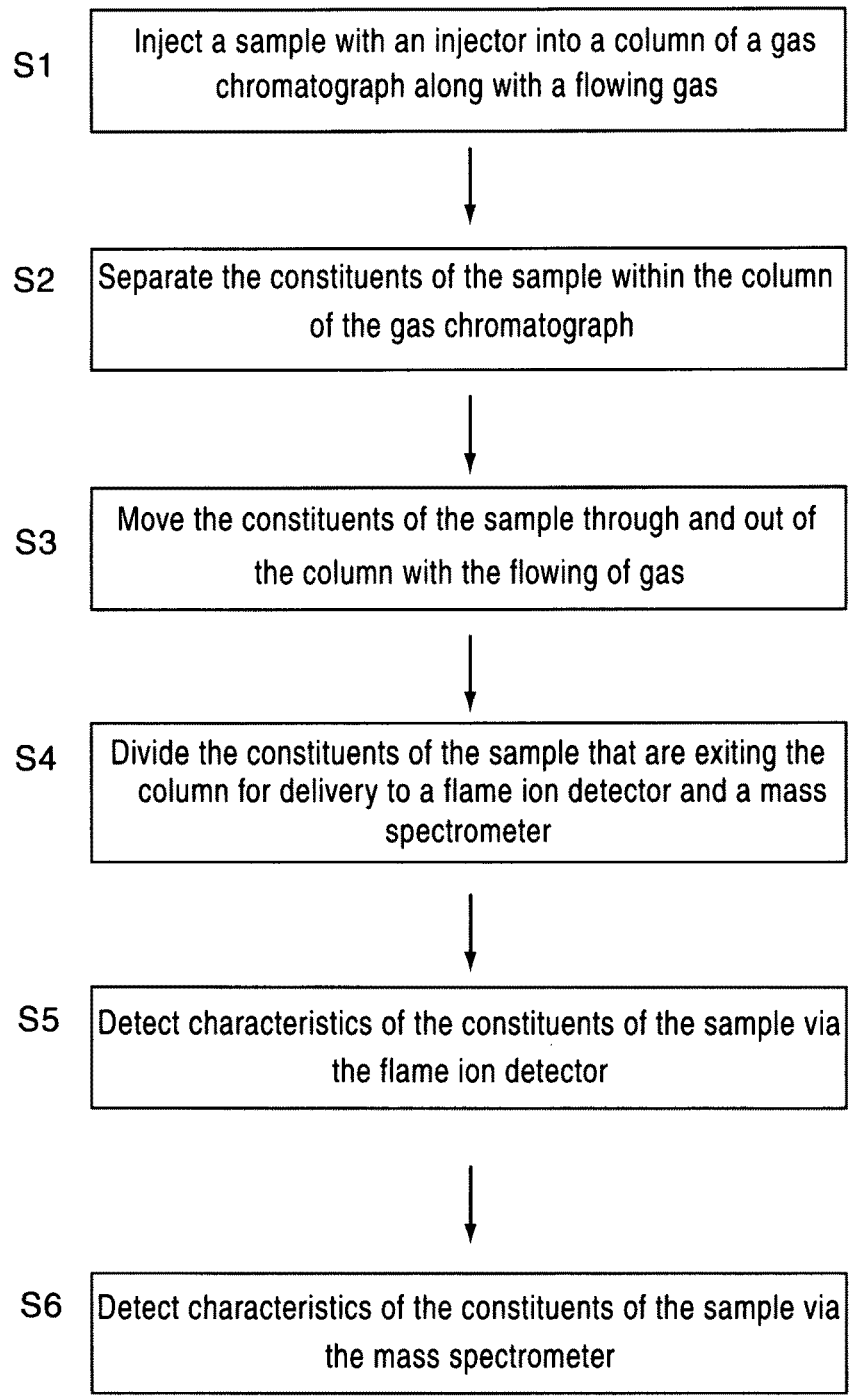
FIG. 3B shows a flow chart of an exemplary method according to an embodiment of the present invention.

FIG. 3B shows a flow chart according to a method in accordance with an embodiment of the present invention. In step S1, a sample to be analyzed is injected into a column of a gas chromatograph along with a flowing gas via an injector. In step S2, the constituents of the sample are separated within the column of the gas chromatograph. In step S3, the constituents are moved through and out of the column with the flowing gas. In step S4, the constituents of the sample are divided as the constituents exit the column. The divided constituents are supplied to a flame ion detector and a mass spectrometer. According to various exemplary embodiments, the sample is divided via a divider, and the constituents are heated at a temperature necessary to ensure that there is no molecule discrimination between the supply of constituents to the mass spectrometer and the supply of constituents to the flame ion detector. Thus, the portion of the constituents that is sent to the mass spectrometer and the portion of the constituents that is sent to the flame ion detector are approximately equal, and the integrity of the constituents is preserved. In step S5, the characteristics of the constituents of the sample are detected via the flame ion detector. In step S6, the characteristics of the constituents of the sample are detected via the mass spectrometer. It should be noted that although steps S5 and S6 describe the detection via the mass spectrometer occurring before the detection via the flame ion detector, the order could be reversed, or the detection via both the mass spectrometer and the flame ion detector can take place at the same time. After the characteristics are detected, the data may be acquired and processed by a data processing system. The accumulated data from both detectors obtained from continuous equal time slice analysis is stored for subsequent processing.

Yields and compositions, in terms of the boiling point distributions and hydrocarbon type breakdowns across the boiling range of interest, may be determined. In addition, changes in chemical compositions and yields in upgrading and/or conversion processes may be analyzed and studied.

Among other things, the present invention may be used to establish a preliminary evaluation of a variety of geochemical parameters or biomarkers for the correlation to fingerprint identification, maturity, origins, etc., of crude oil or fraction thereof that is analyzed. Experimental data may be correlated to chemical and physical properties. This enables refining strategies to be planned to maximize yields of required products without affecting their quality. Feedstocks can be rapidly tested by correlating the composition of products to quality.

In addition, the distribution and type of sulphur compounds in distillates may be determined. The profile and quantities of heterocompounds in distillates may be studied by coupling specific detectors to the apparatus.

Figure 4:
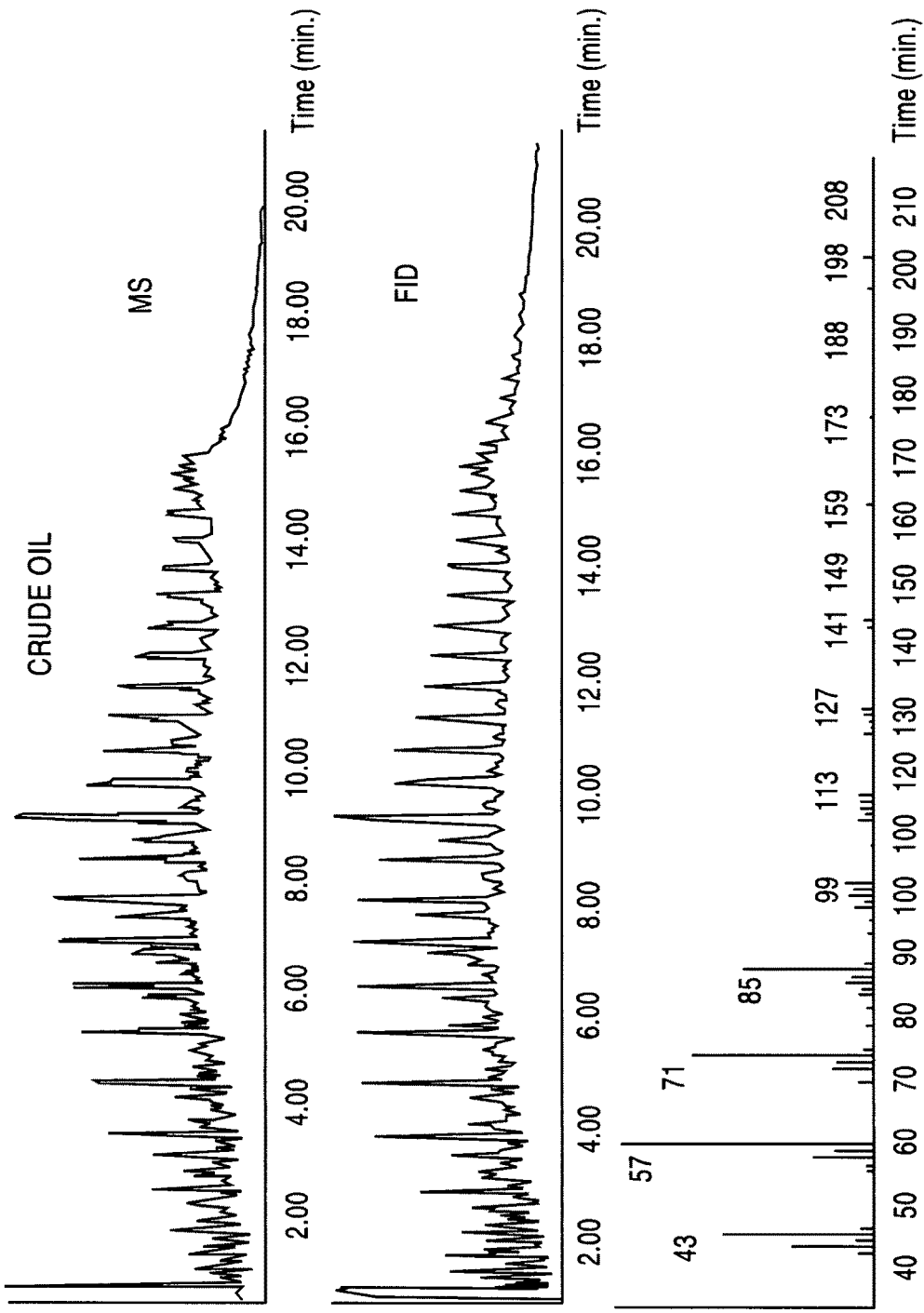
FIG. 4 shows the results of a sample analyzed in accordance with a method and system of an embodiment of the present invention.

Exemplary results produced using application of the present invention to crude oil is shown in FIG. 4. FIG. 4 shows the multidimensionality of the information that may be gathered. FIG. 4 also shows the results detected by the MS, the results detected by the FID, and the combined information.

Figure 5:
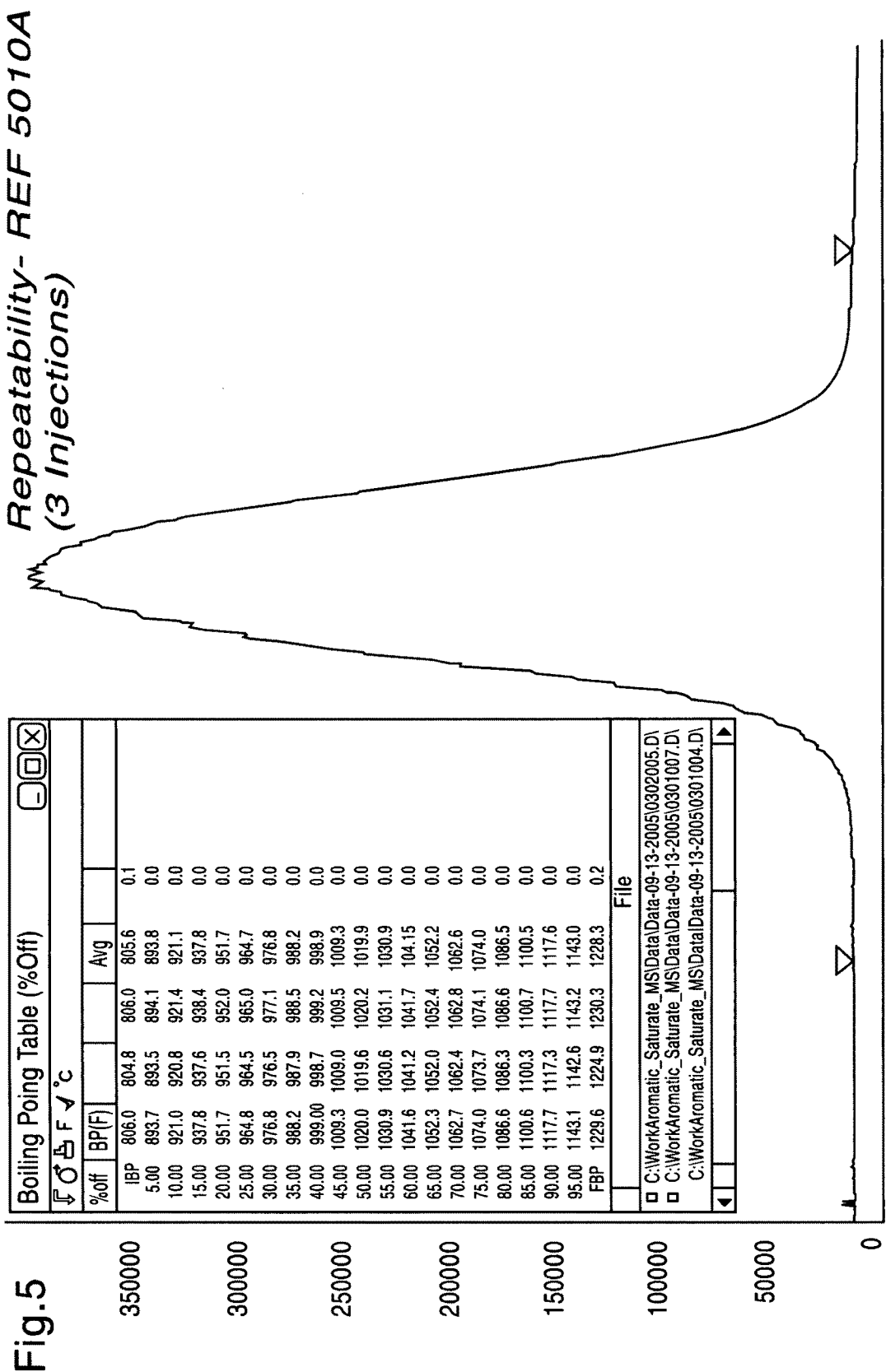
FIG. 5 shows results for three injections of a similar material analyzed according to a method and system of an embodiment of the present invention.
Figure 6:
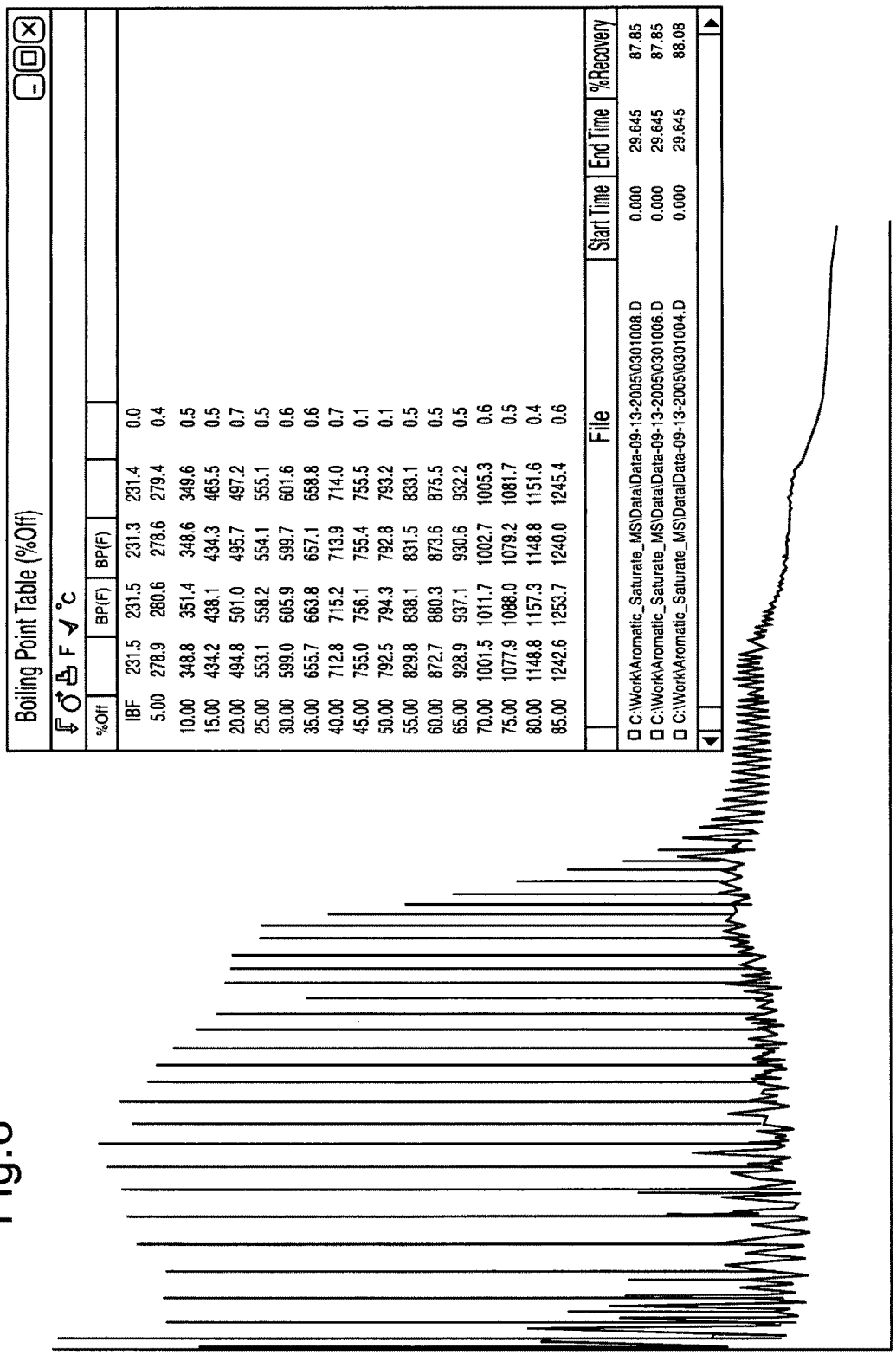
FIG. 6 shows results for three injections of a similar material analyzed according to a method and system of an embodiment of the present invention.

The present invention is fast, with high repeatability, as shown in FIGS. 5 and 6. FIG. 5 shows the results for 3 injections, with one axis showing the signal intensity and the other showing time. The three results nearly overlap each other. The actual values for the three injections are shown in the boiling point table. FIG. 6 shows another set of results for three injections of paraffinic crude oil, produced using a method and system in accordance with an embodiment of the present invention. Thus, the present invention can serve as an excellent screening technique to study the efficiency of physical distillations and refining processes and can rapidly establish the main compositional characteristics of crude oils, so that their quality for decision making purposes can be quickly established. Further, the present invention can serve as part of a quick exploration tool to establish the principle characteristics of crude oil quality allowing for decisions on refinement planning and commercialization.

Figure 7:
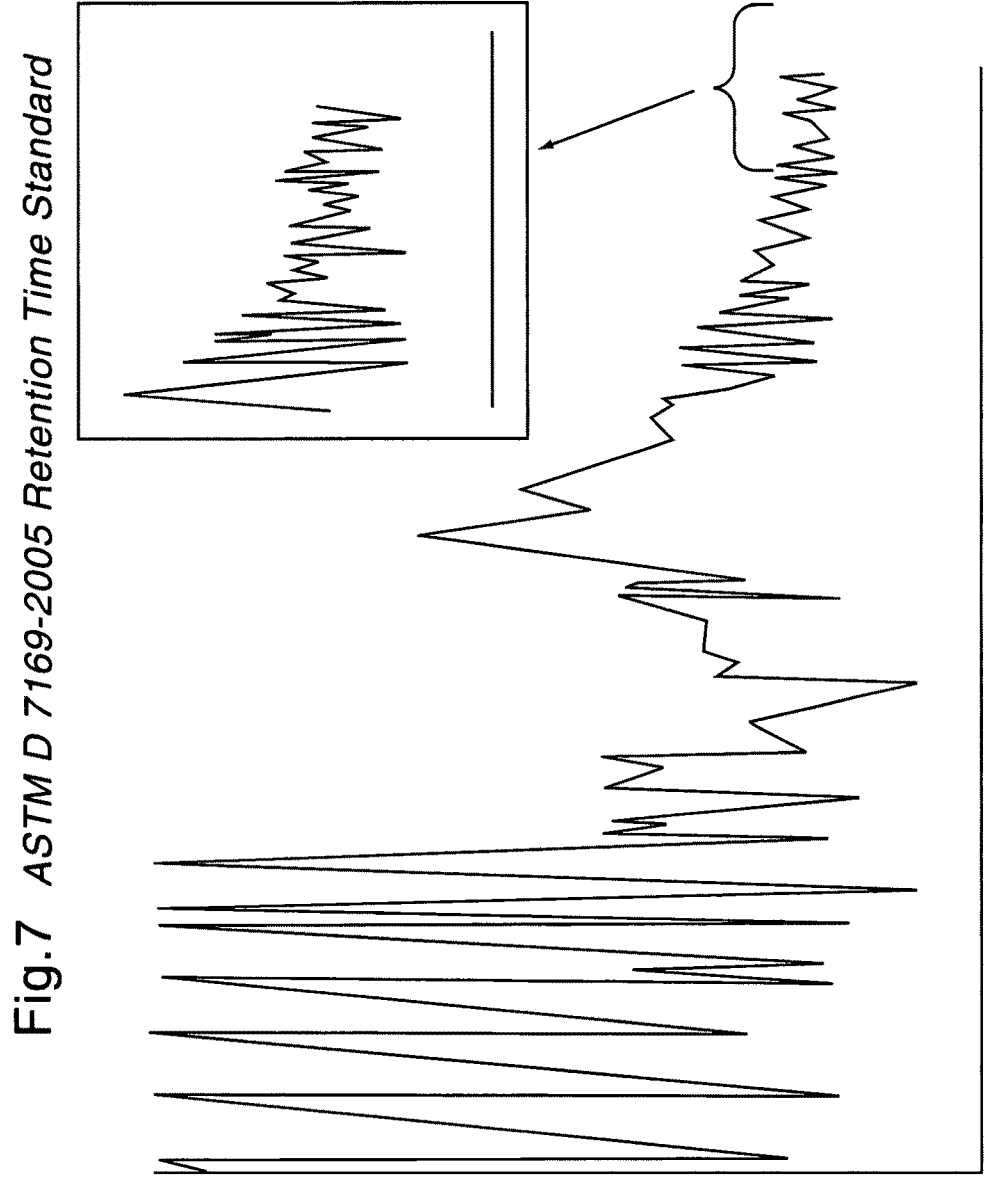
FIG. 7 shows a retention time standard for ASTM D 7169-2005.
Figure 8:
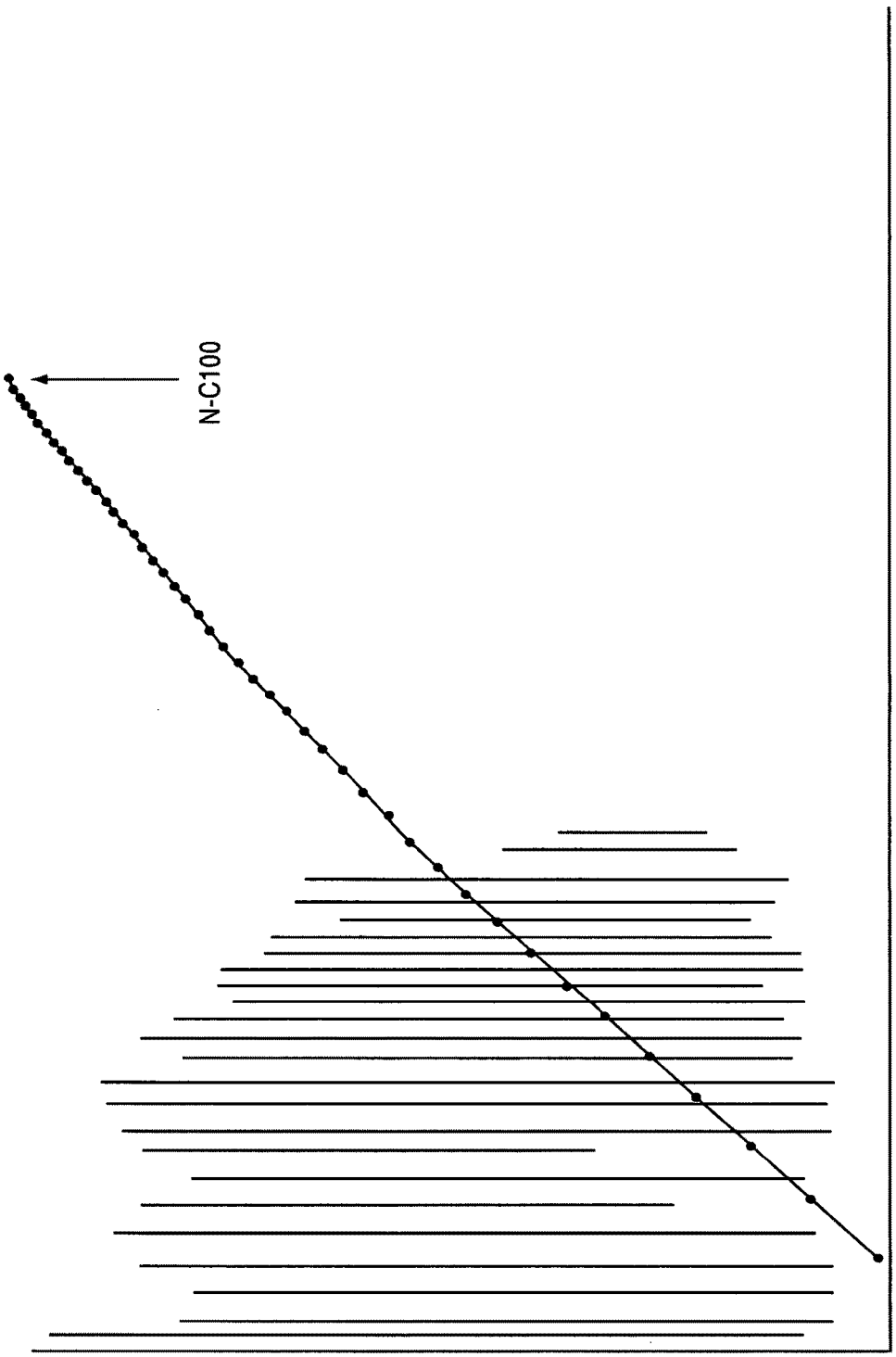
FIG. 8 shows a crude oil boiling point calibration curve.
Figure 9:
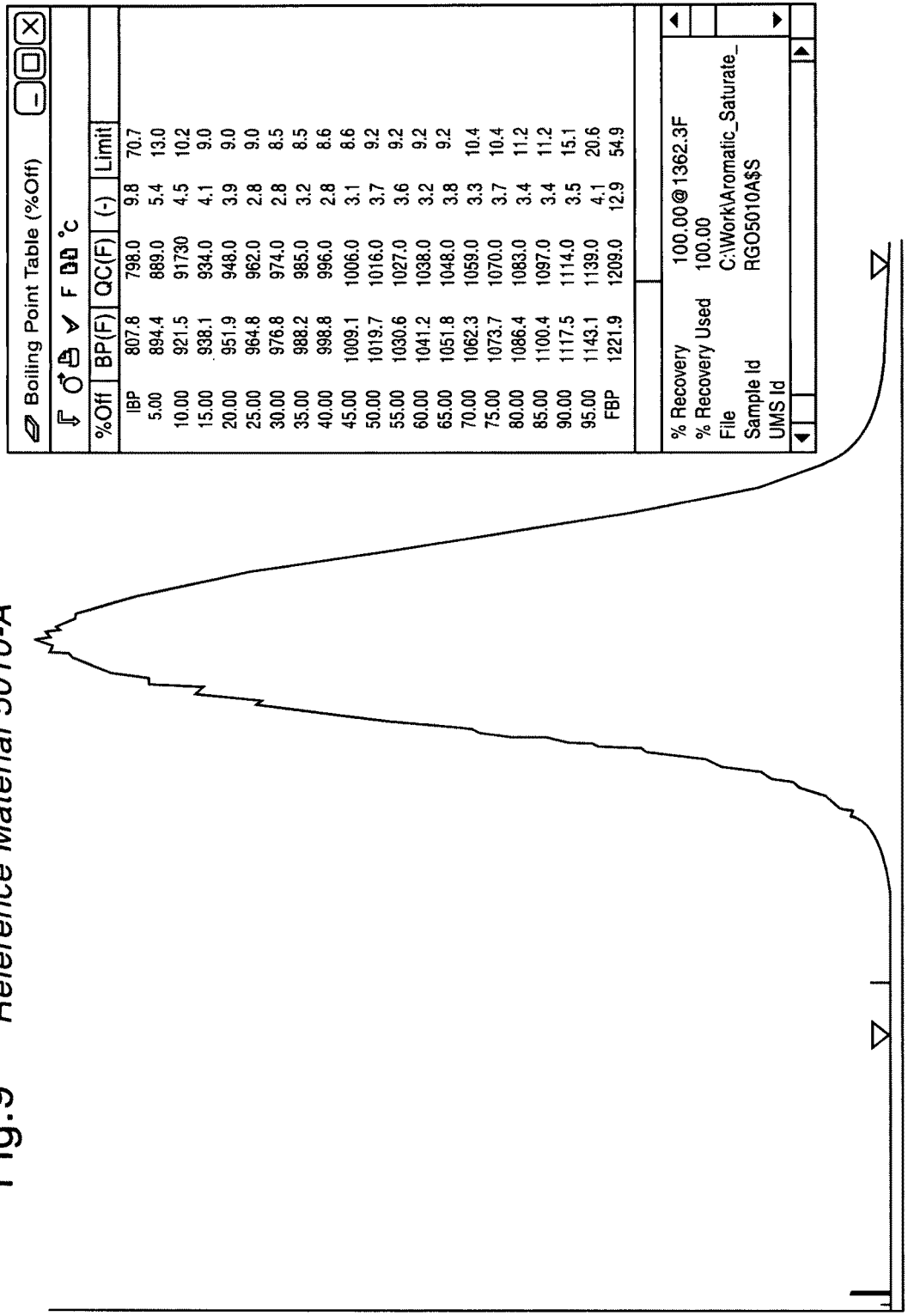
FIG. 9 shows the measured results of a reference material.
Figure 10:
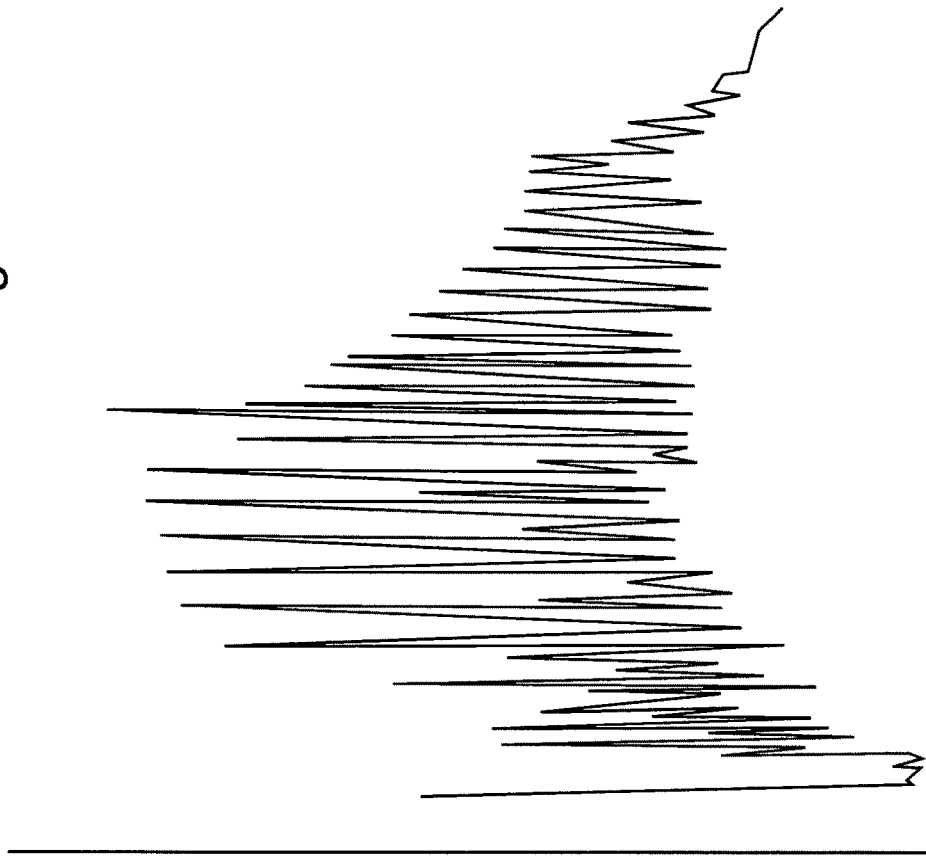
FIG. 10 shows the measured results for a crude oil sample.
Figure 13:
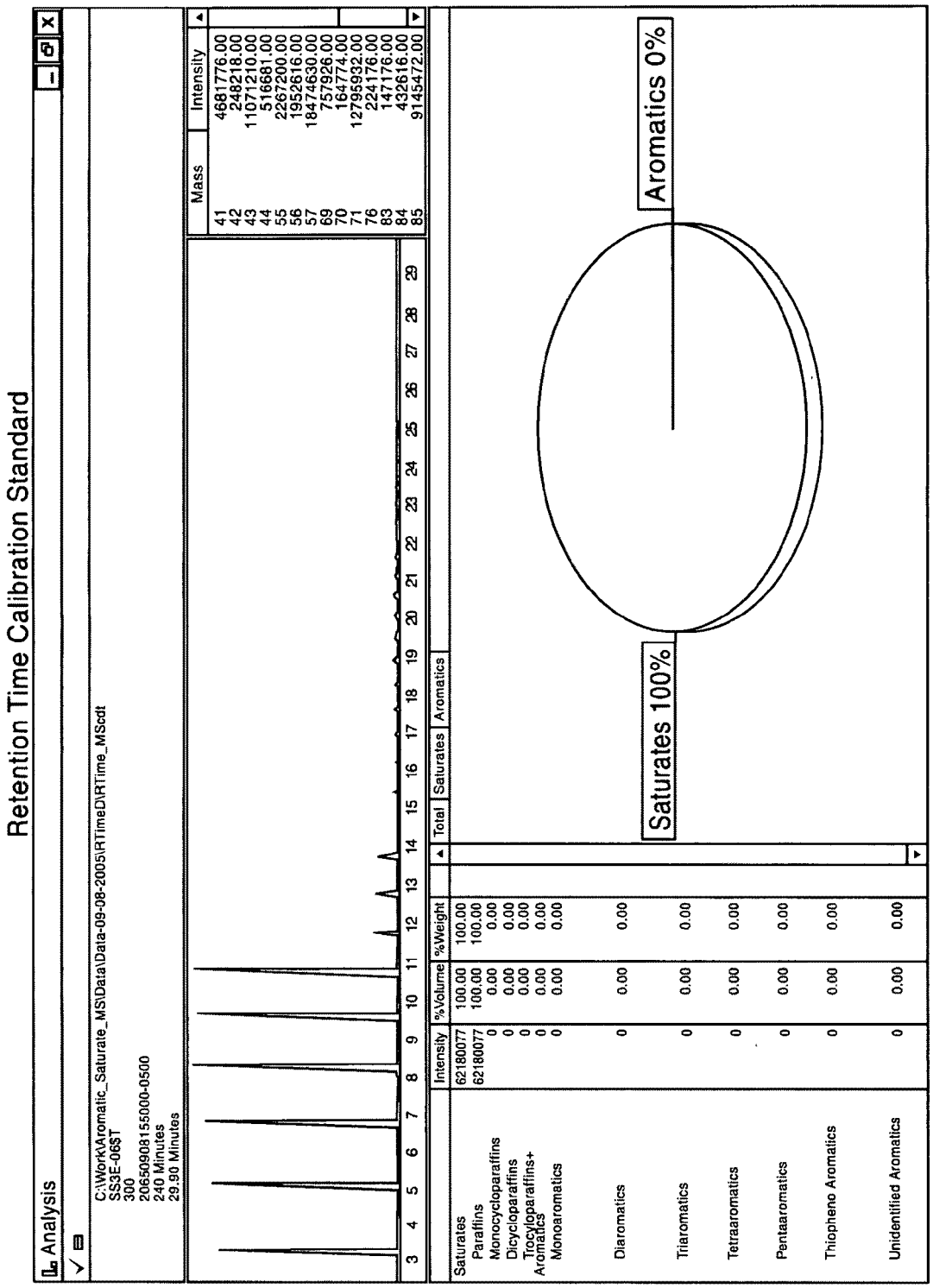
FIG. 13 shows a retention time calibration standard useable in accordance with embodiments of the present invention.
Figure 14:
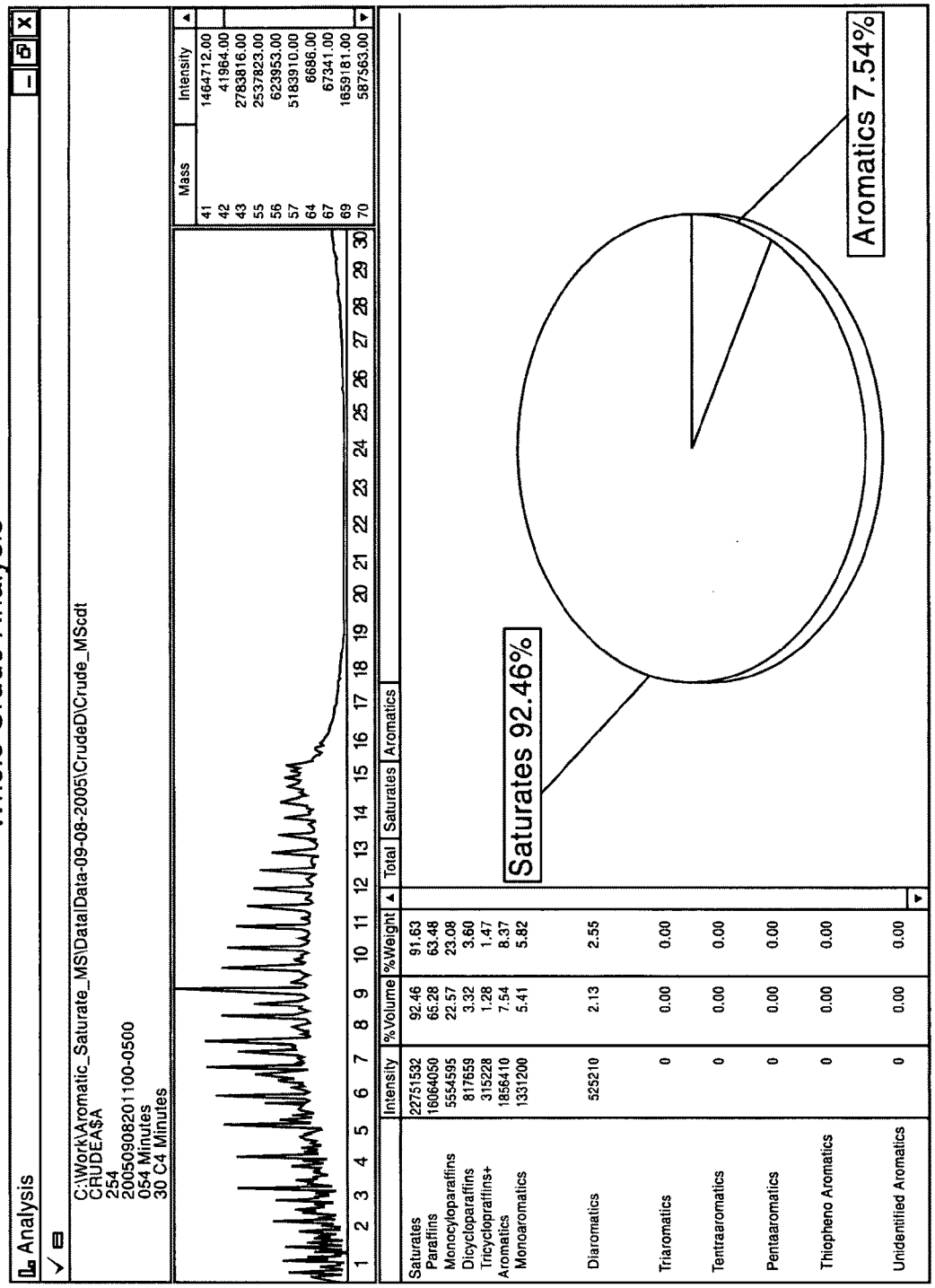
FIG. 14 shows a whole crude oil analysis useable in accordance with embodiments of the present invention.
Figure 15:
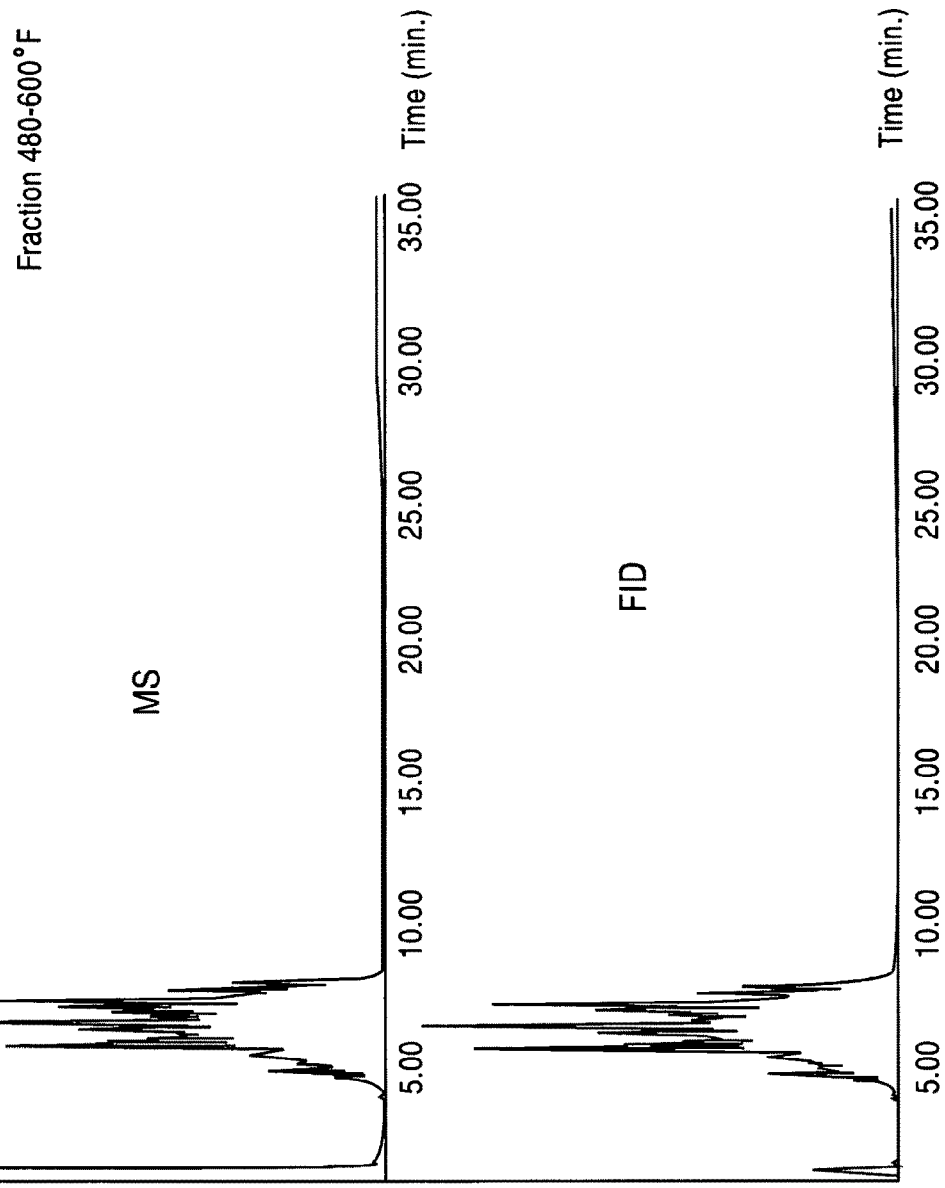
FIG. 15 shows experimental results of a measured fraction analyzed in accordance with methods and systems of embodiments of the present invention.
Figure 16:
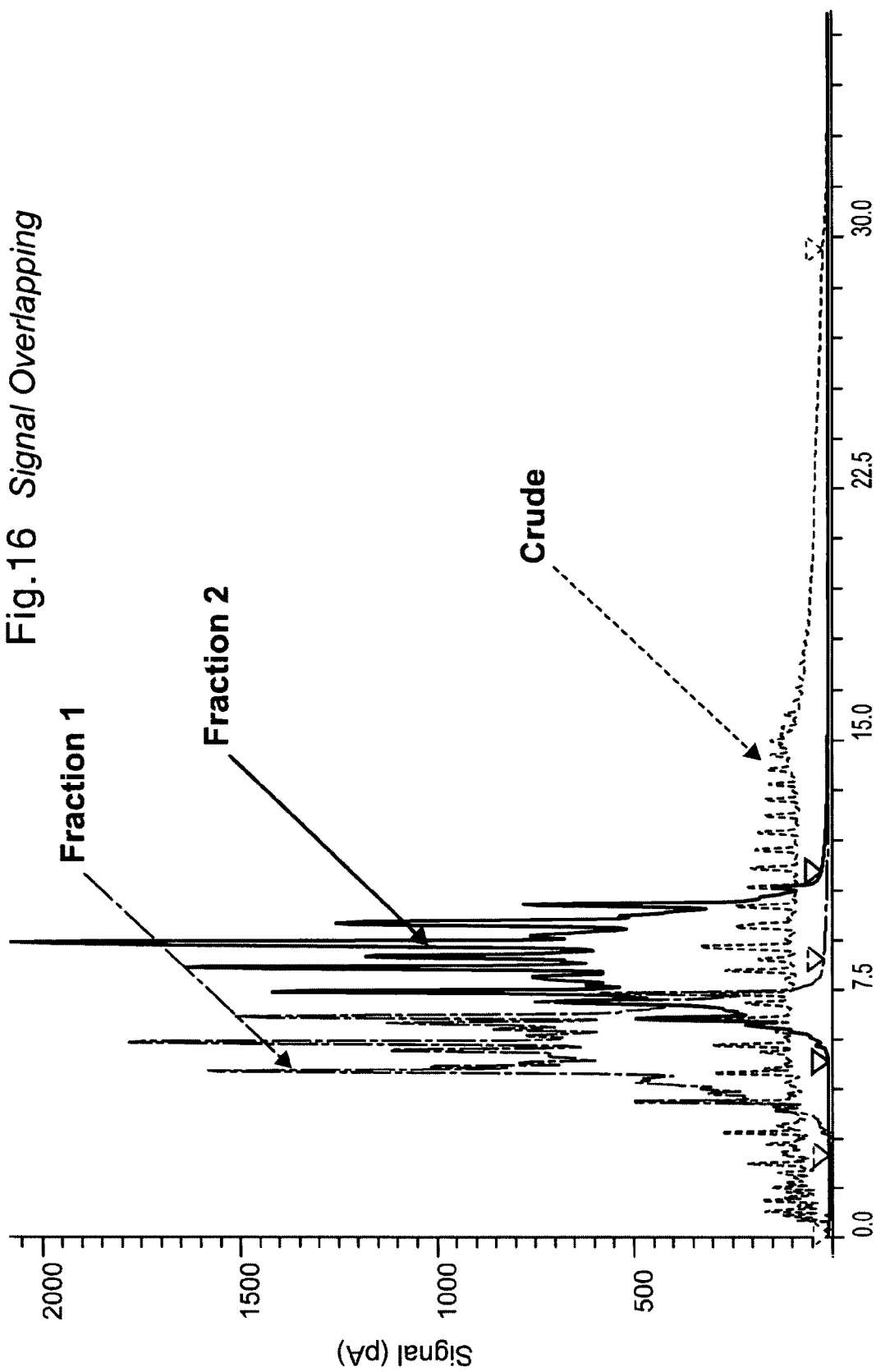
FIG. 16 shows the signal overlapping from fractions, along with crude oil, produced using analysis in accordance with methods and systems of embodiments of the present invention.
Figure 17:
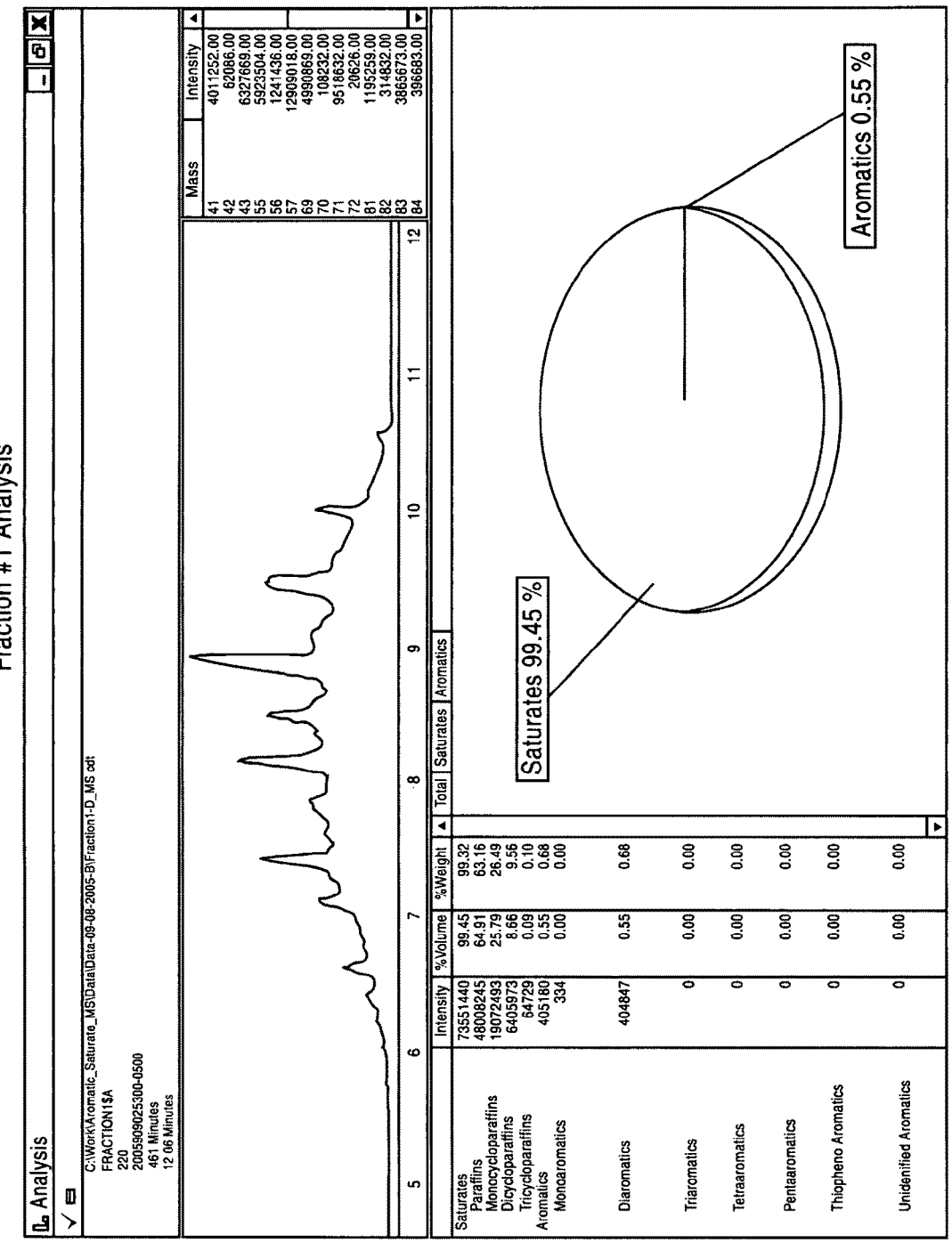
FIG. 17 shows an analysis of Fraction #1, as analyzed according to a method and system of an embodiment of the present invention.
Figure 18:
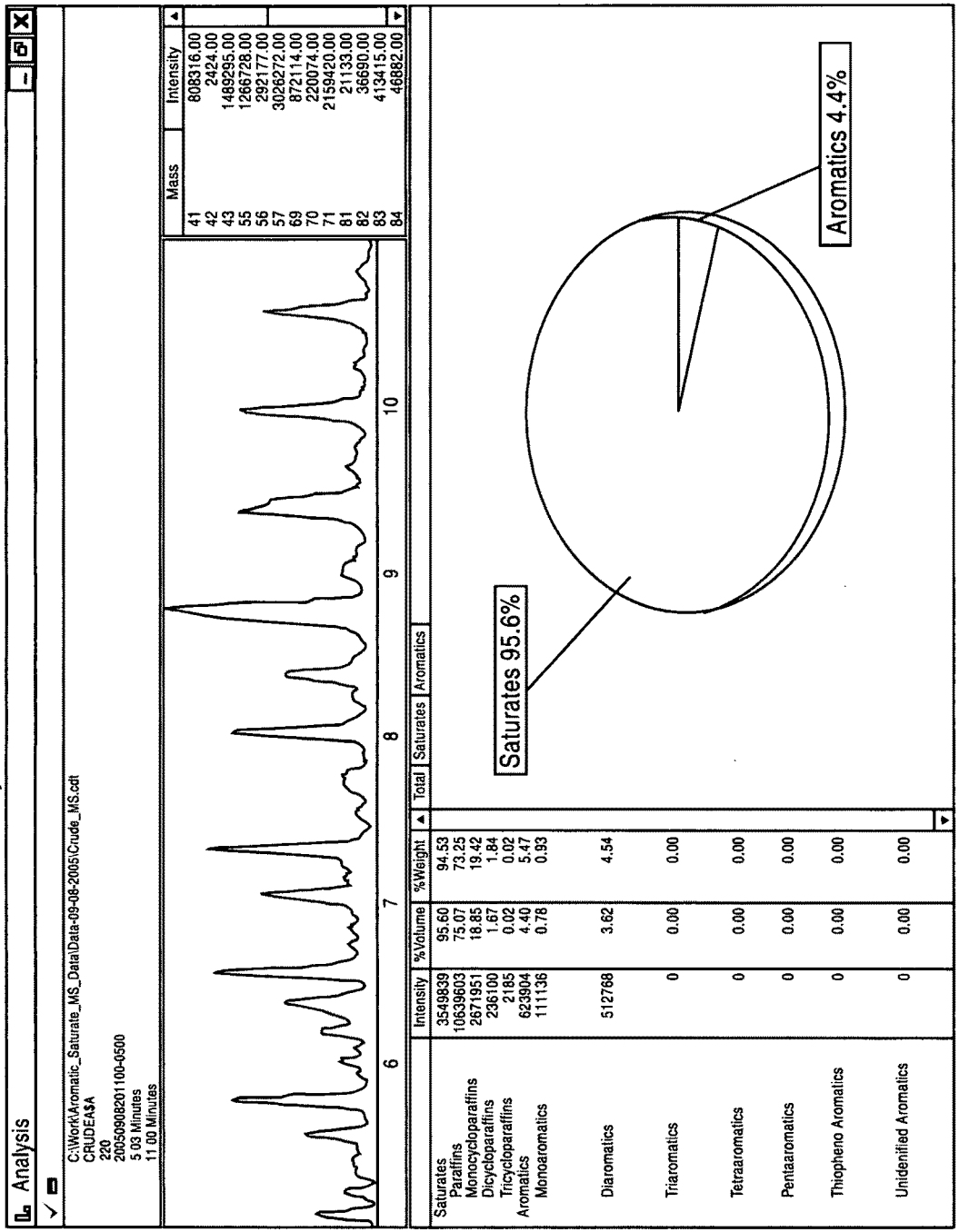
FIG. 18 shows an analysis of Fraction #1 cut in whole crude, as analyzed according to a method and system of an embodiment of the present invention.
Figure 19:
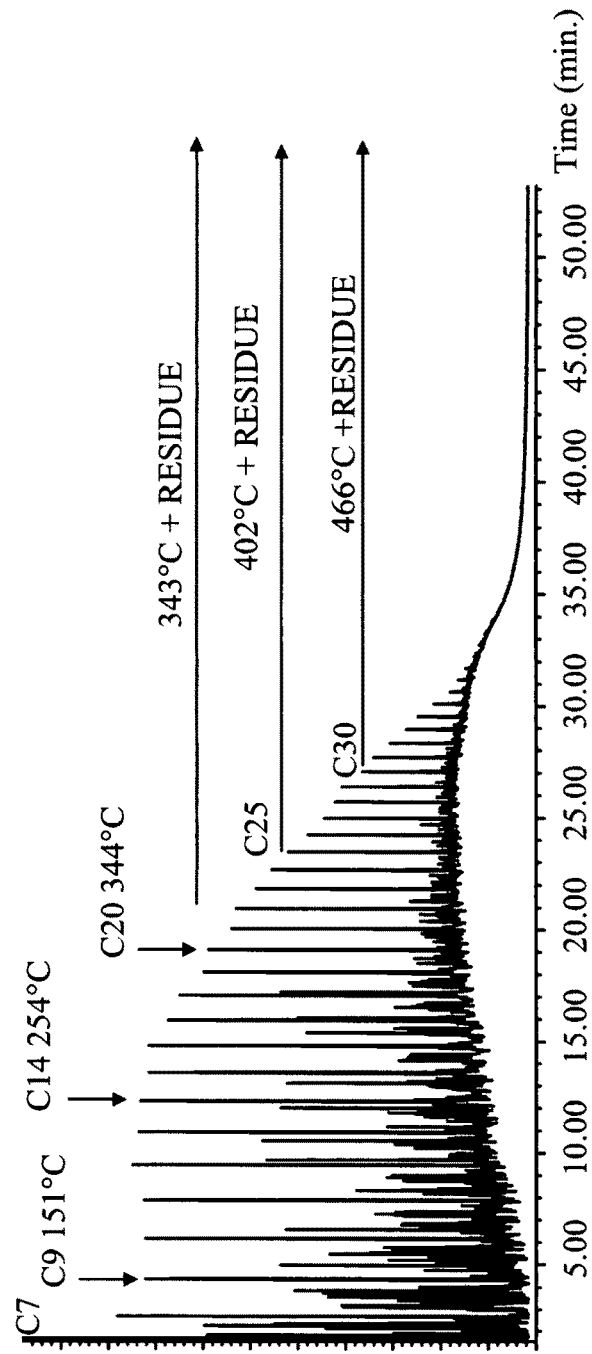
FIG. 19 shows the results of a sample of paraffinic light crude oil, as analyzed according to a method and system of an embodiment of the present invention.
Figure 20:
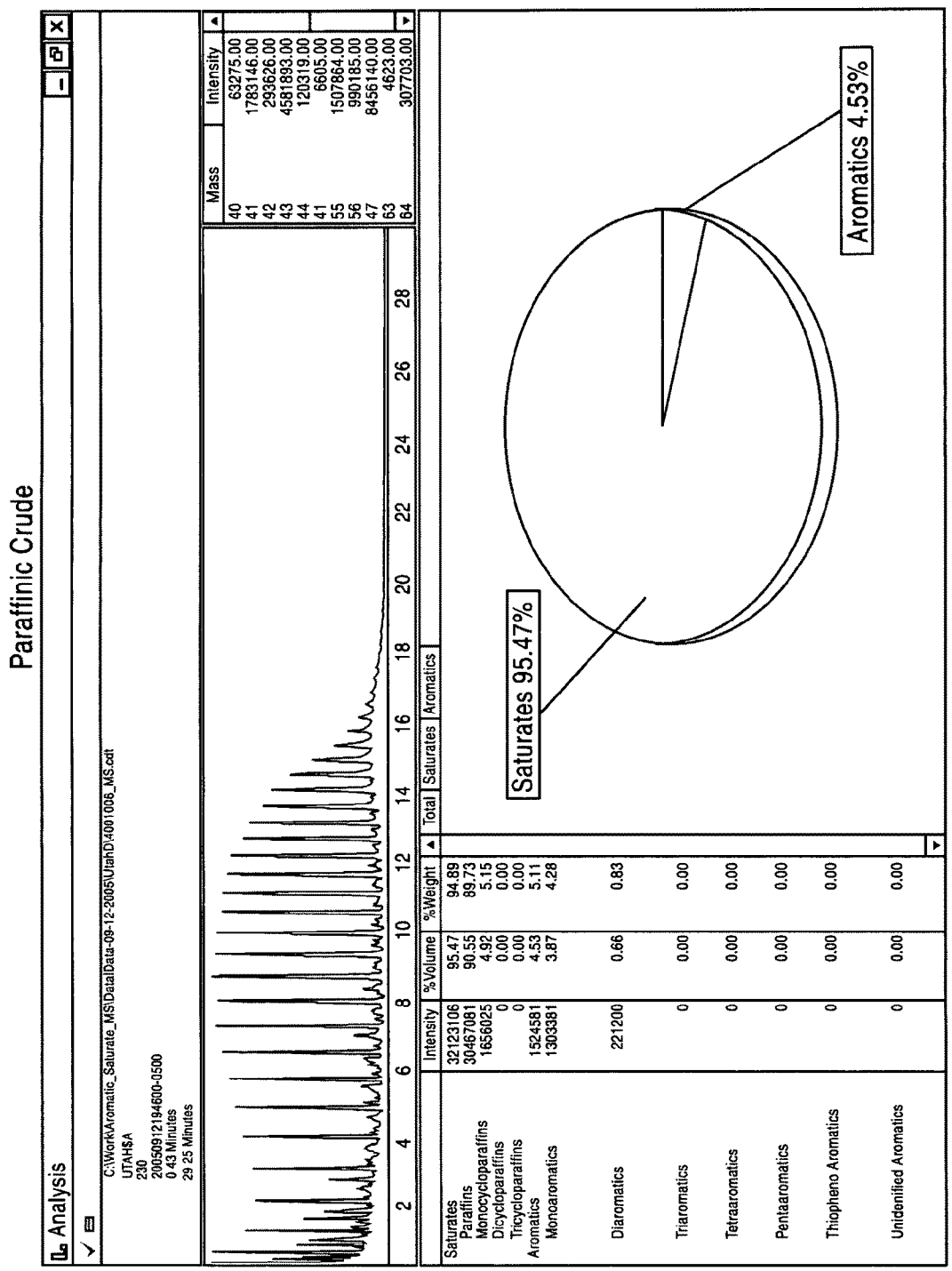
FIG. 20 shows the results of a sample of paraffinic crude oil, as analyzed according to a method and system of an embodiment of the present invention.
Figure 25:
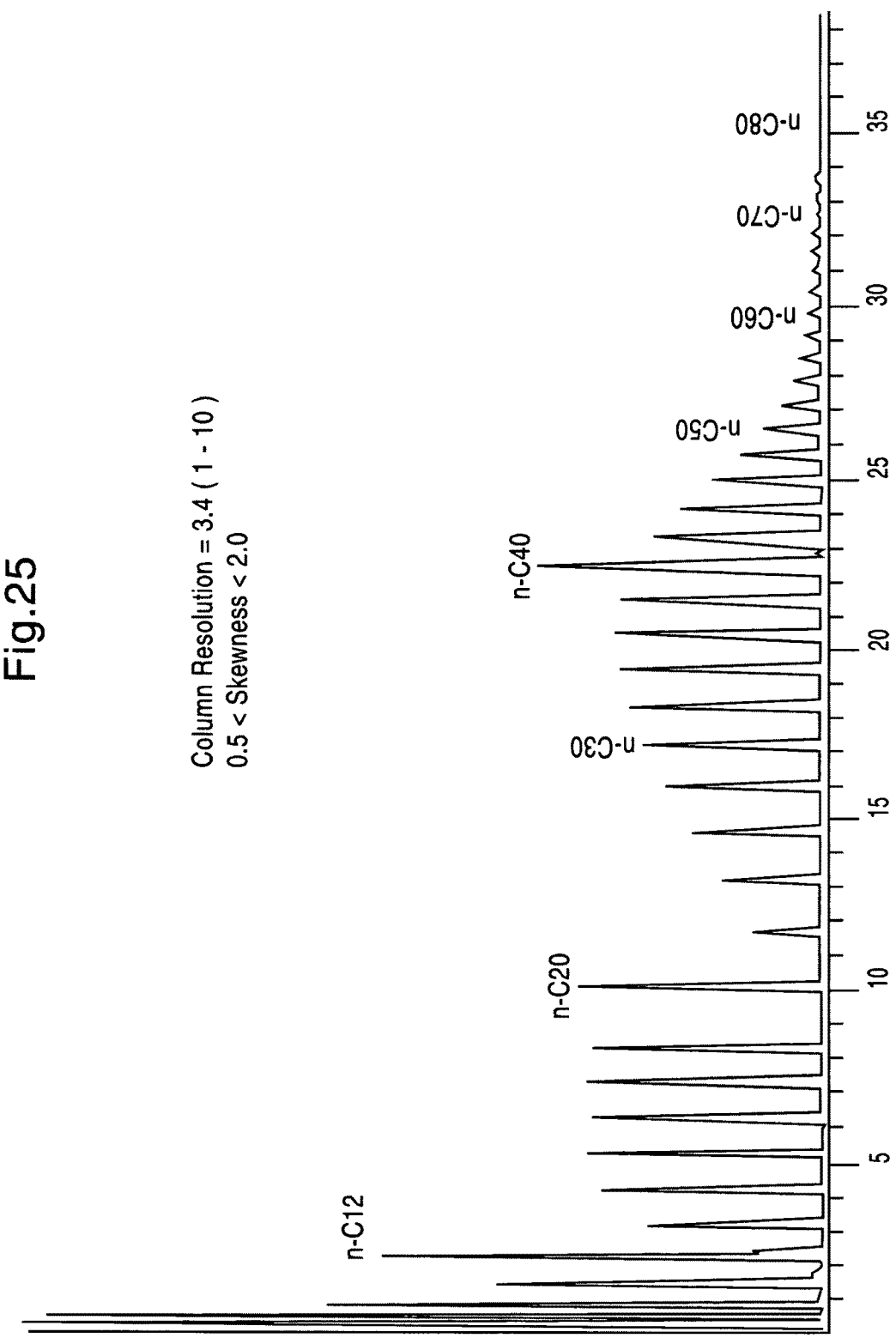
Figure 26:
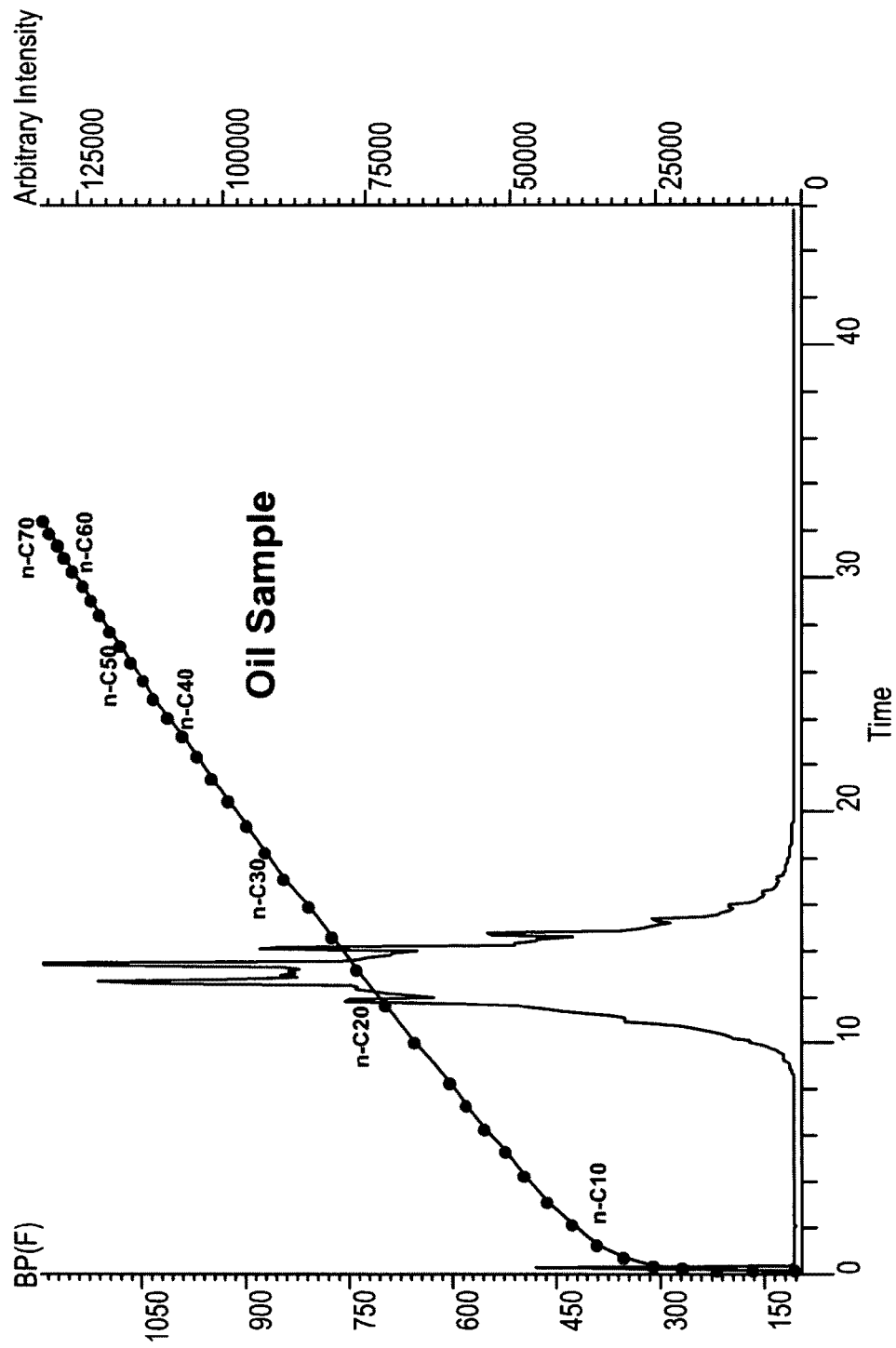
Figure 28:
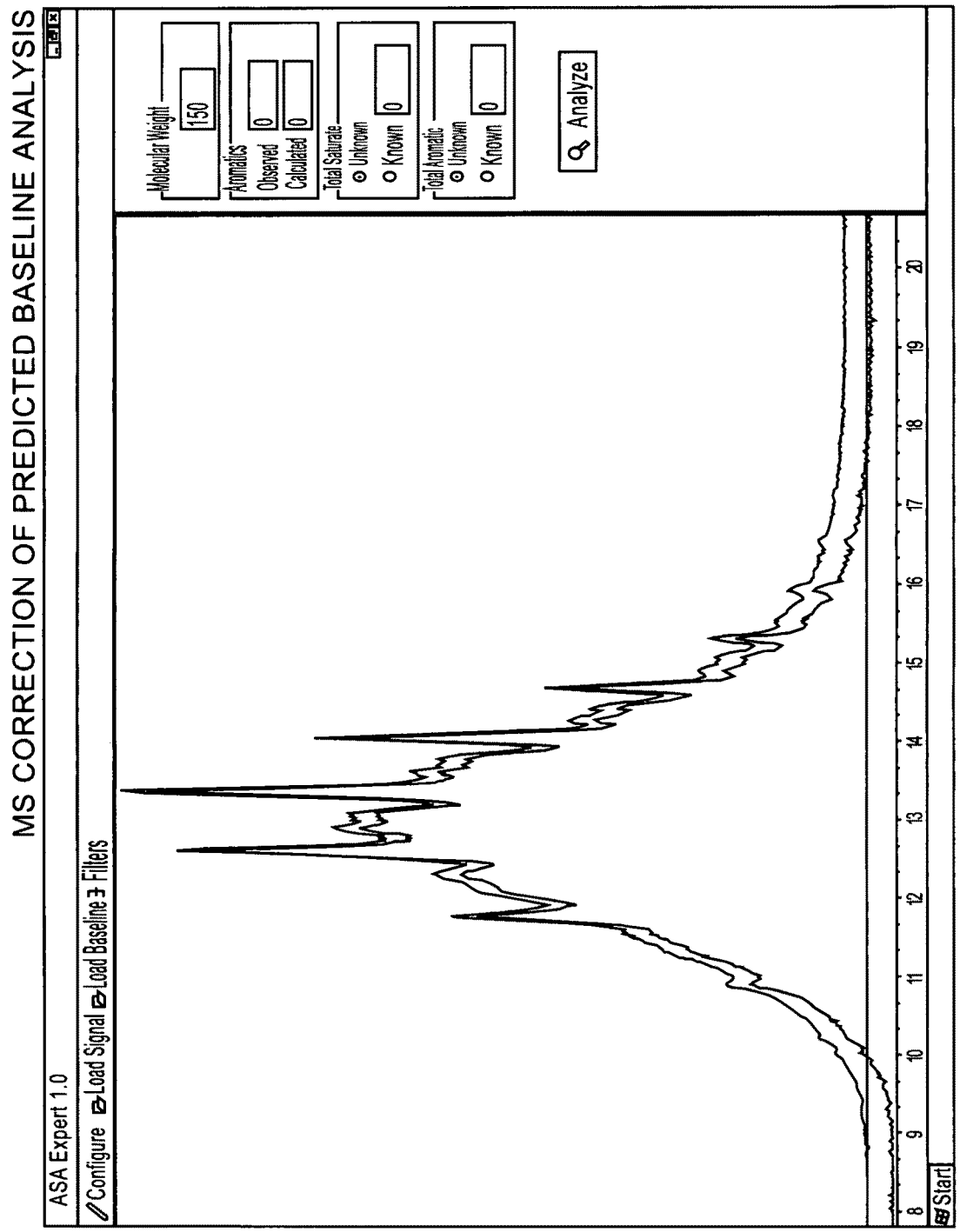
Figure 32:
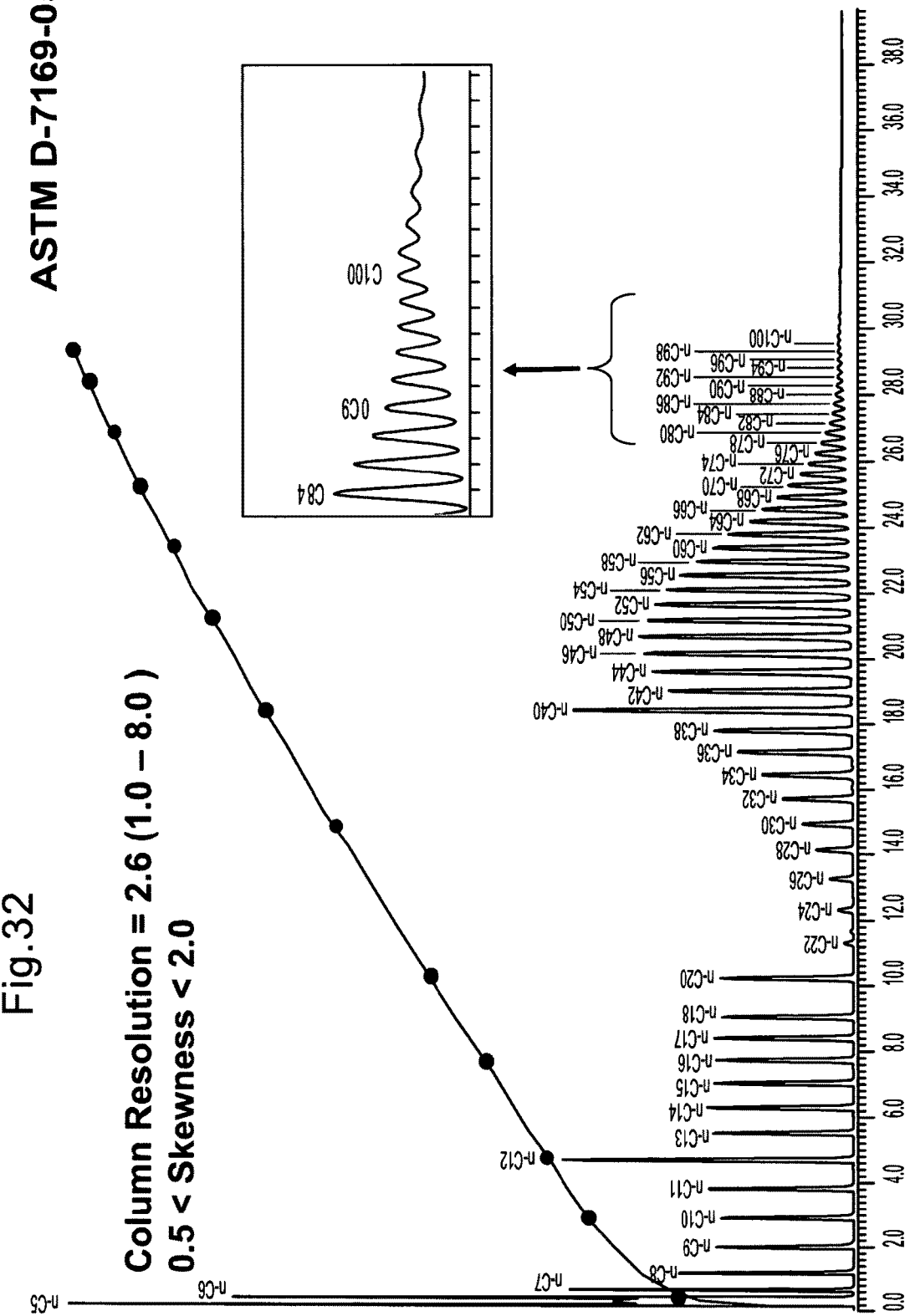
Figure 33:
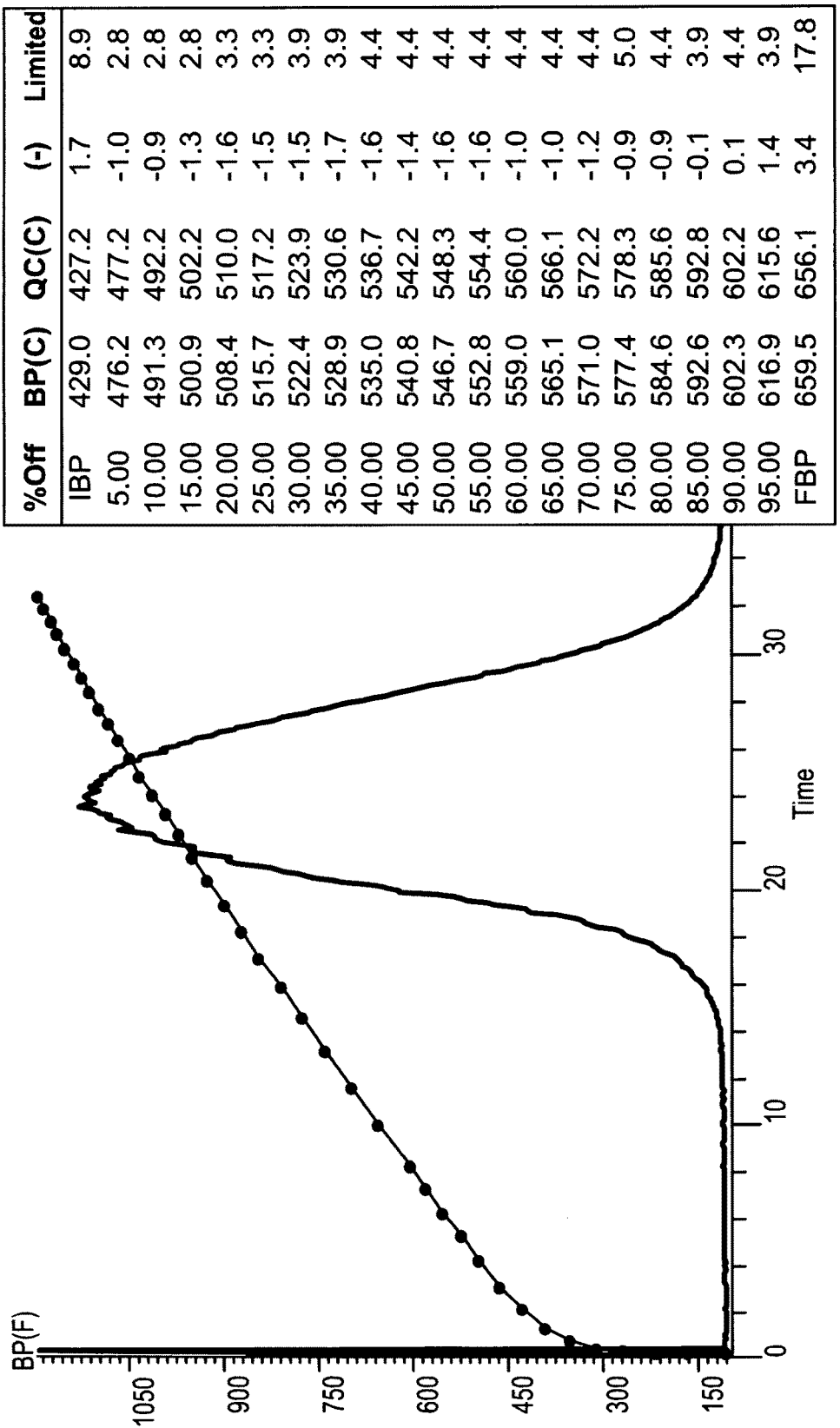
Figure 34:
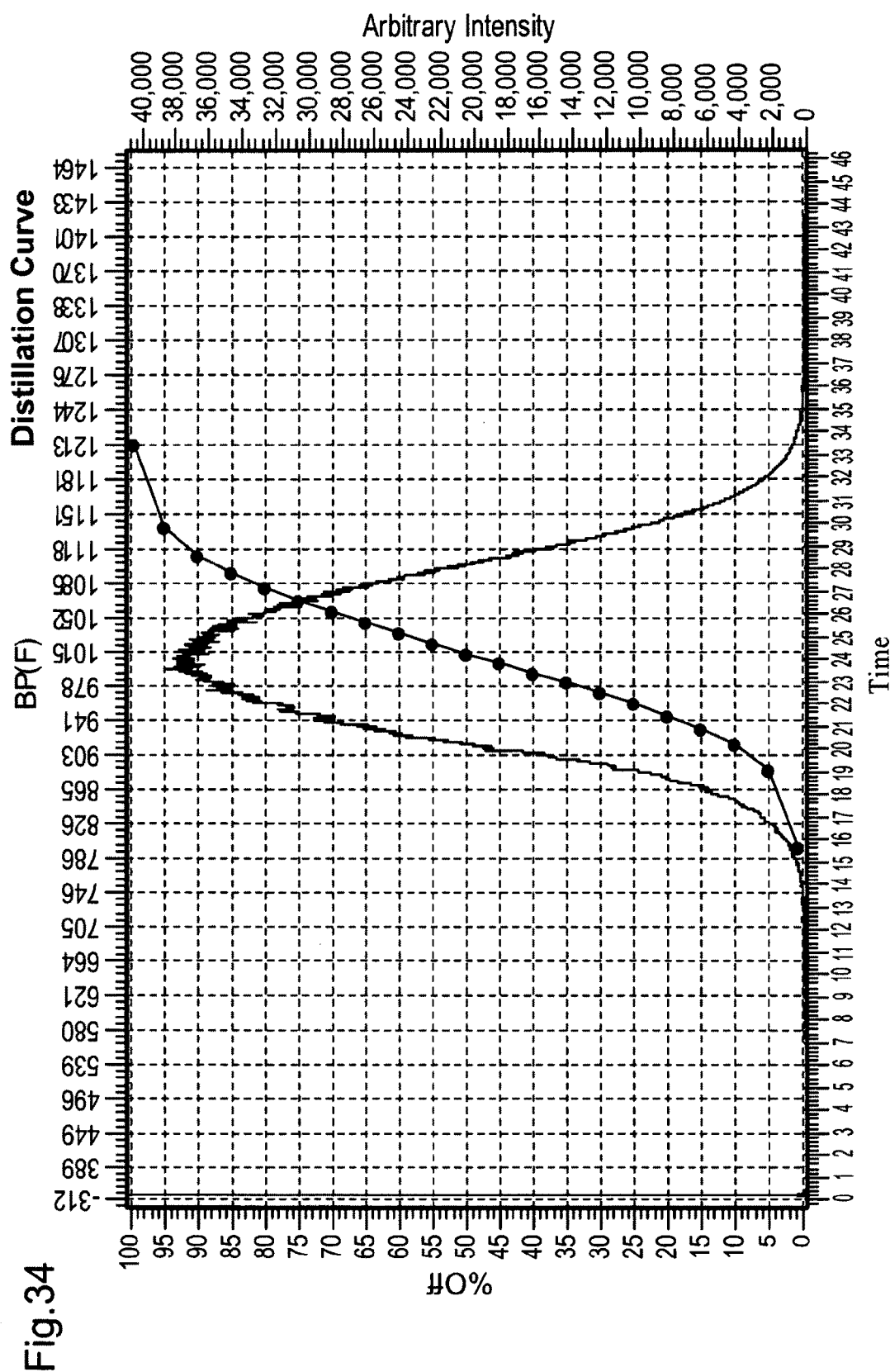
Figure 35:
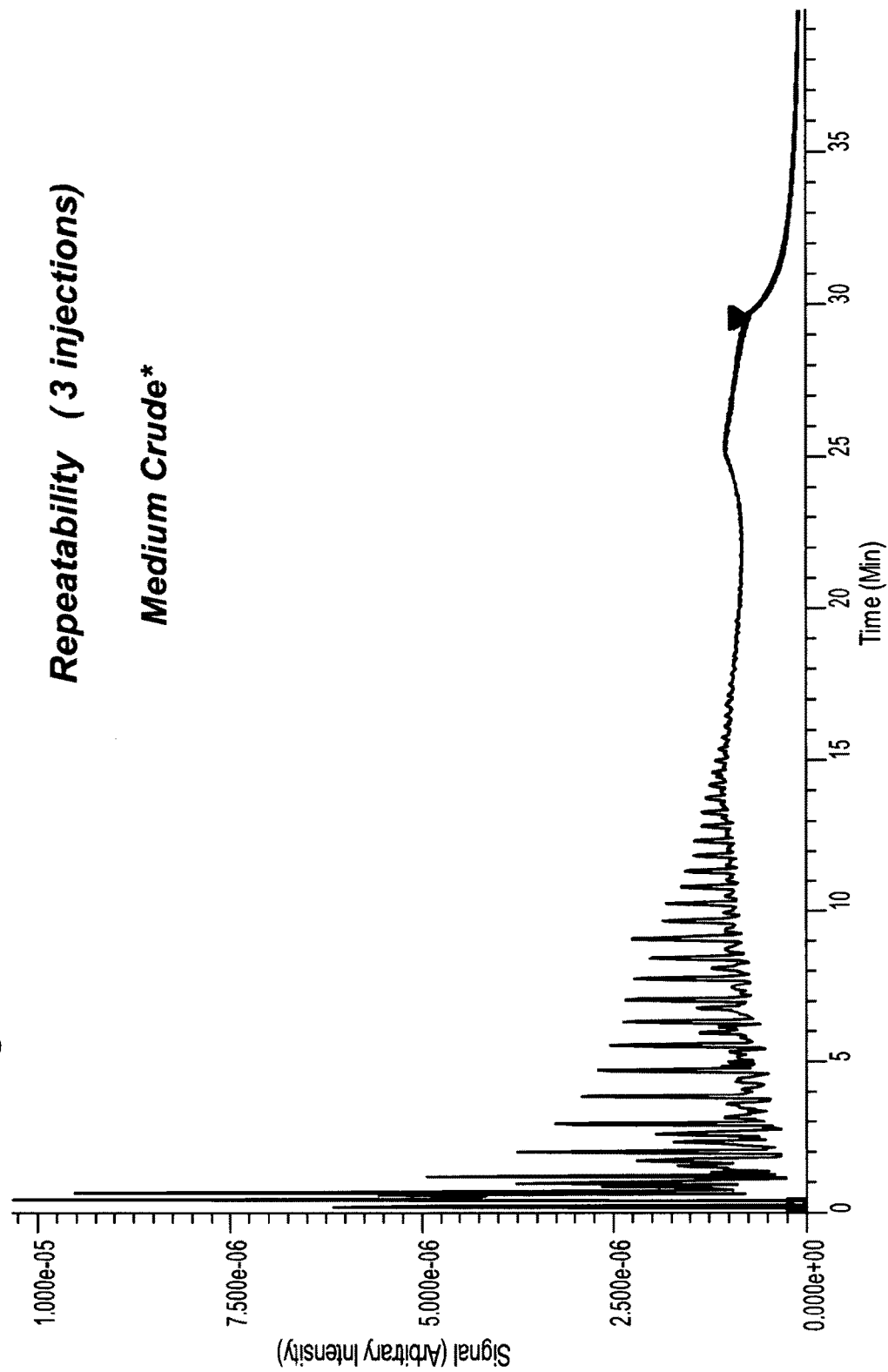
Figure 37:
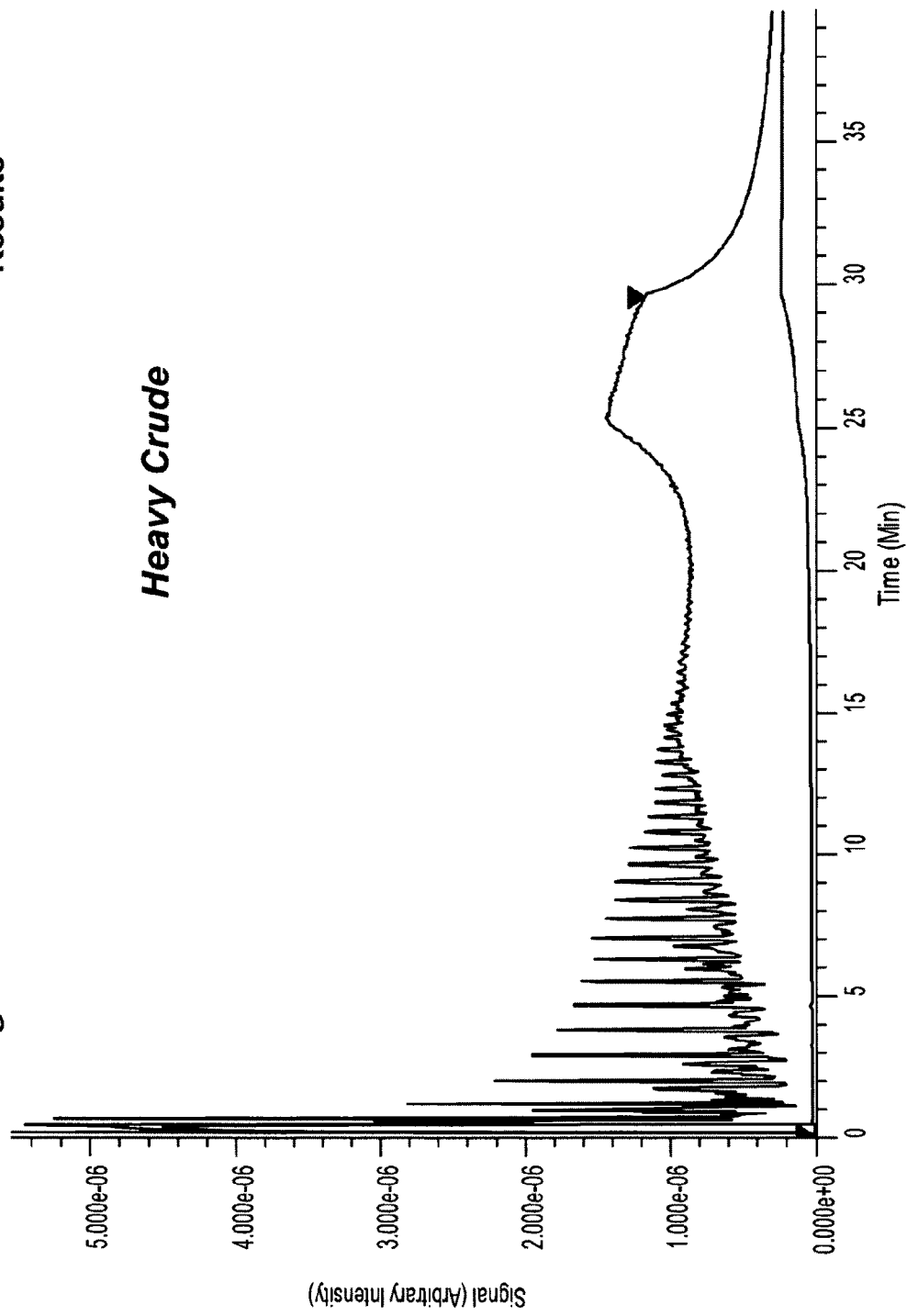
Figure 39:
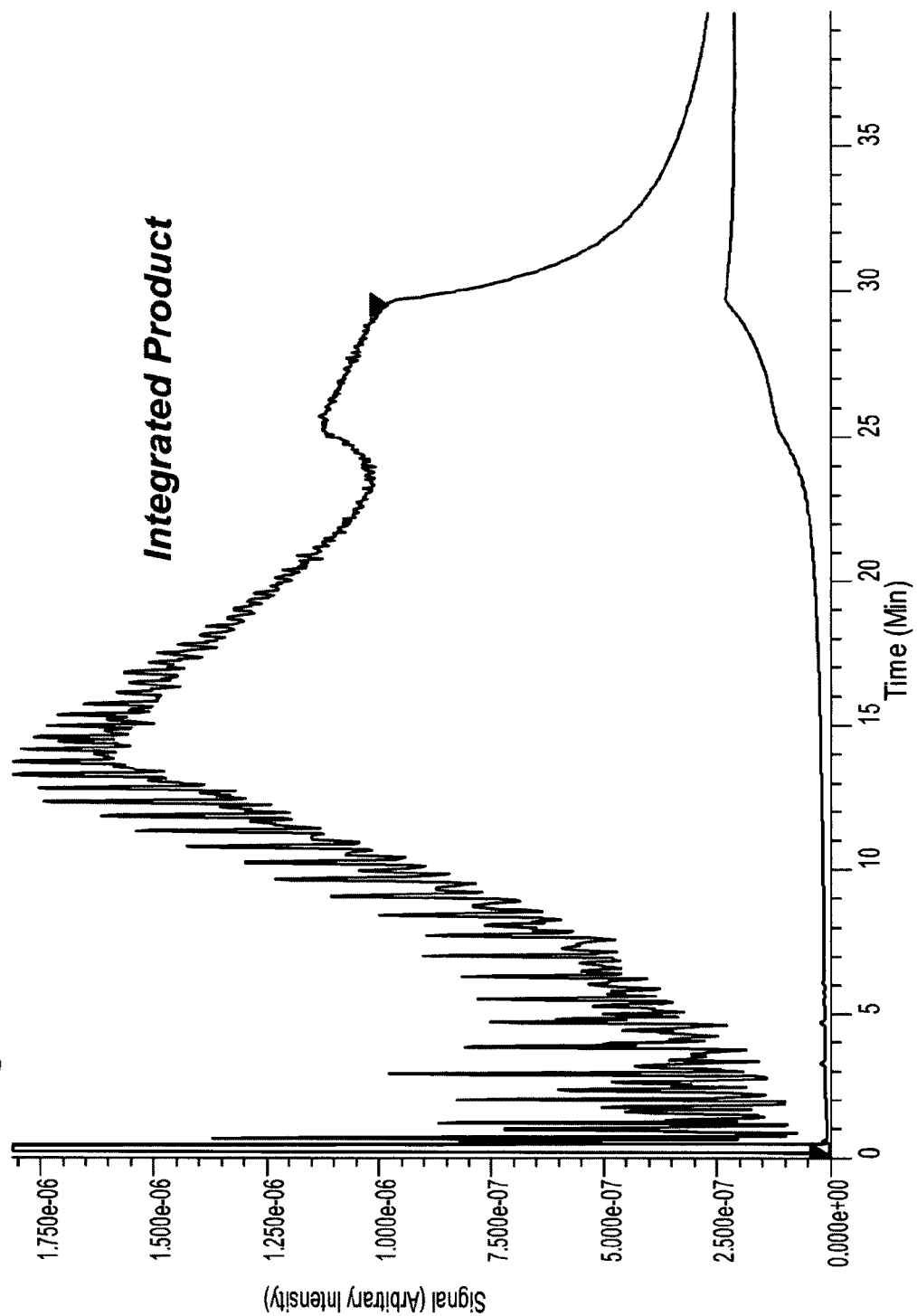
Figure 42:
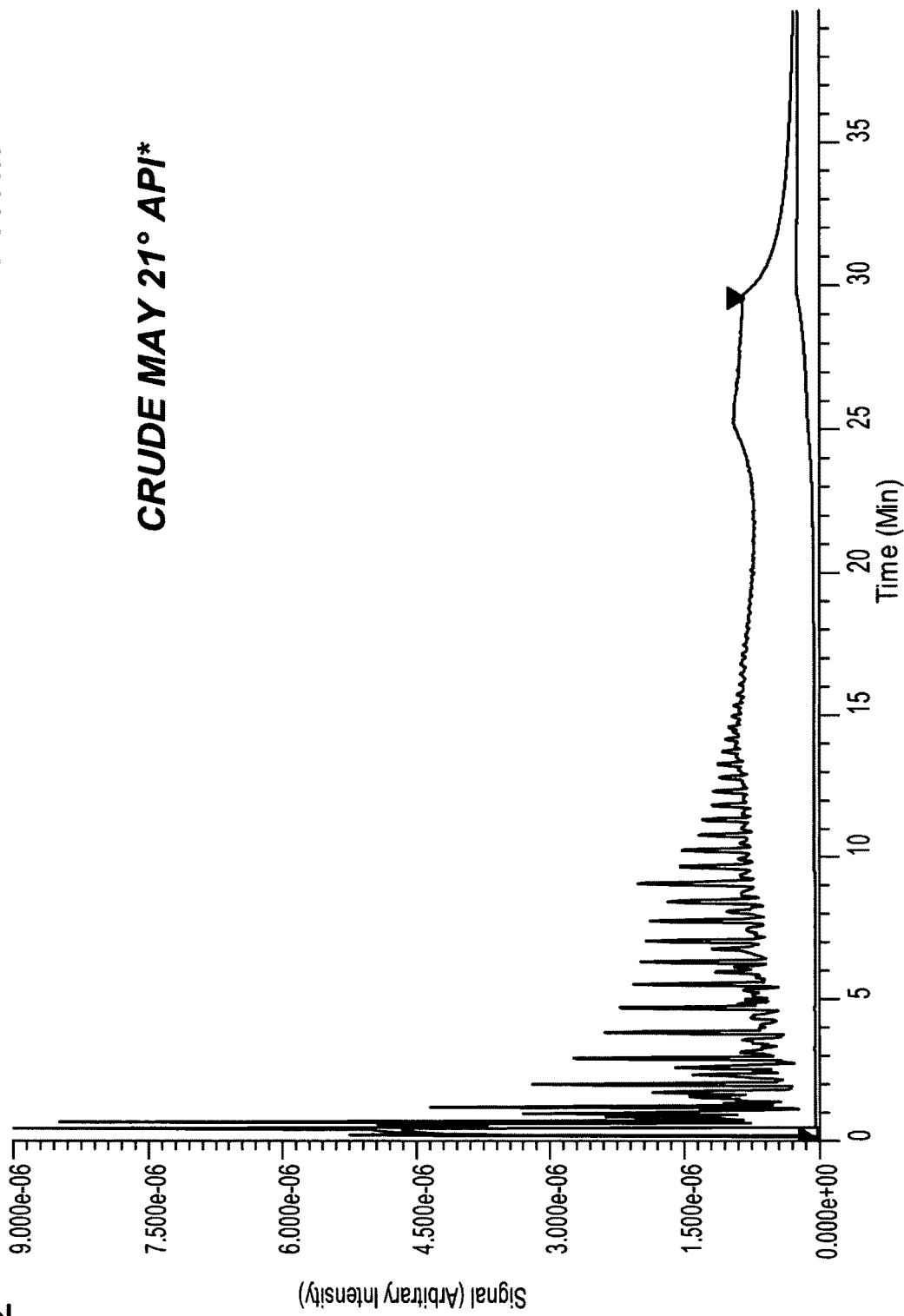
Figure 44:
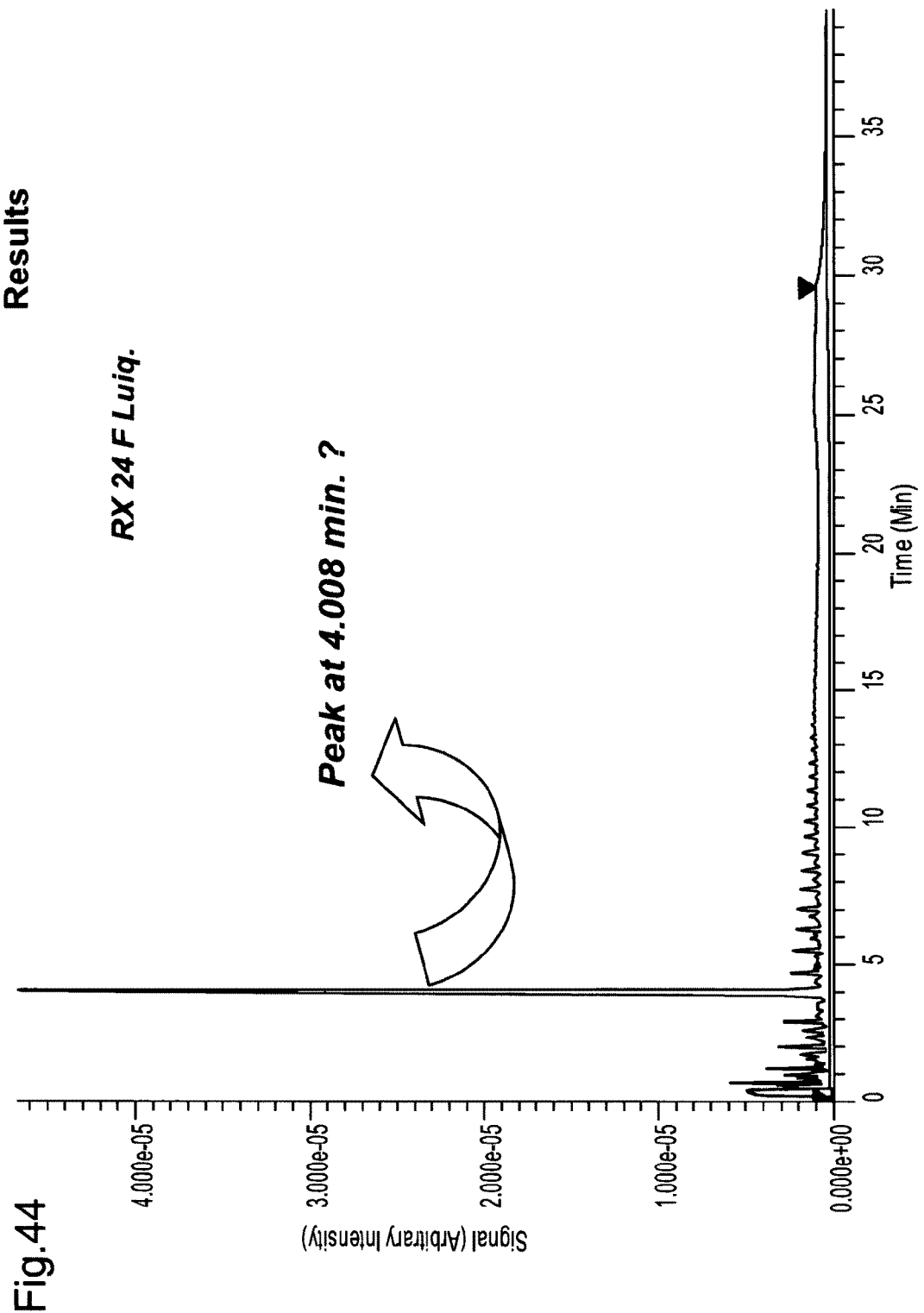
Figure 46:
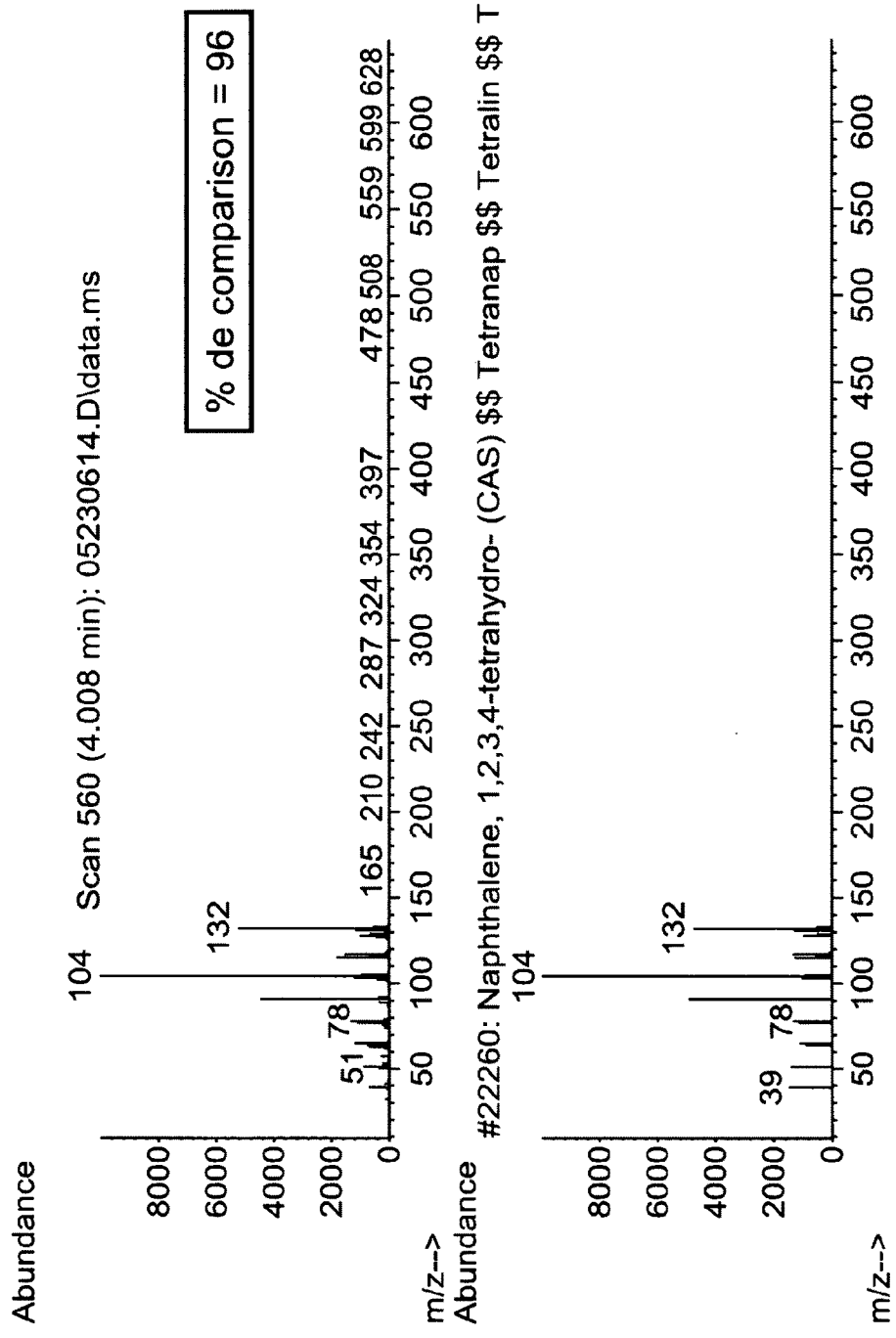
Figure 47:
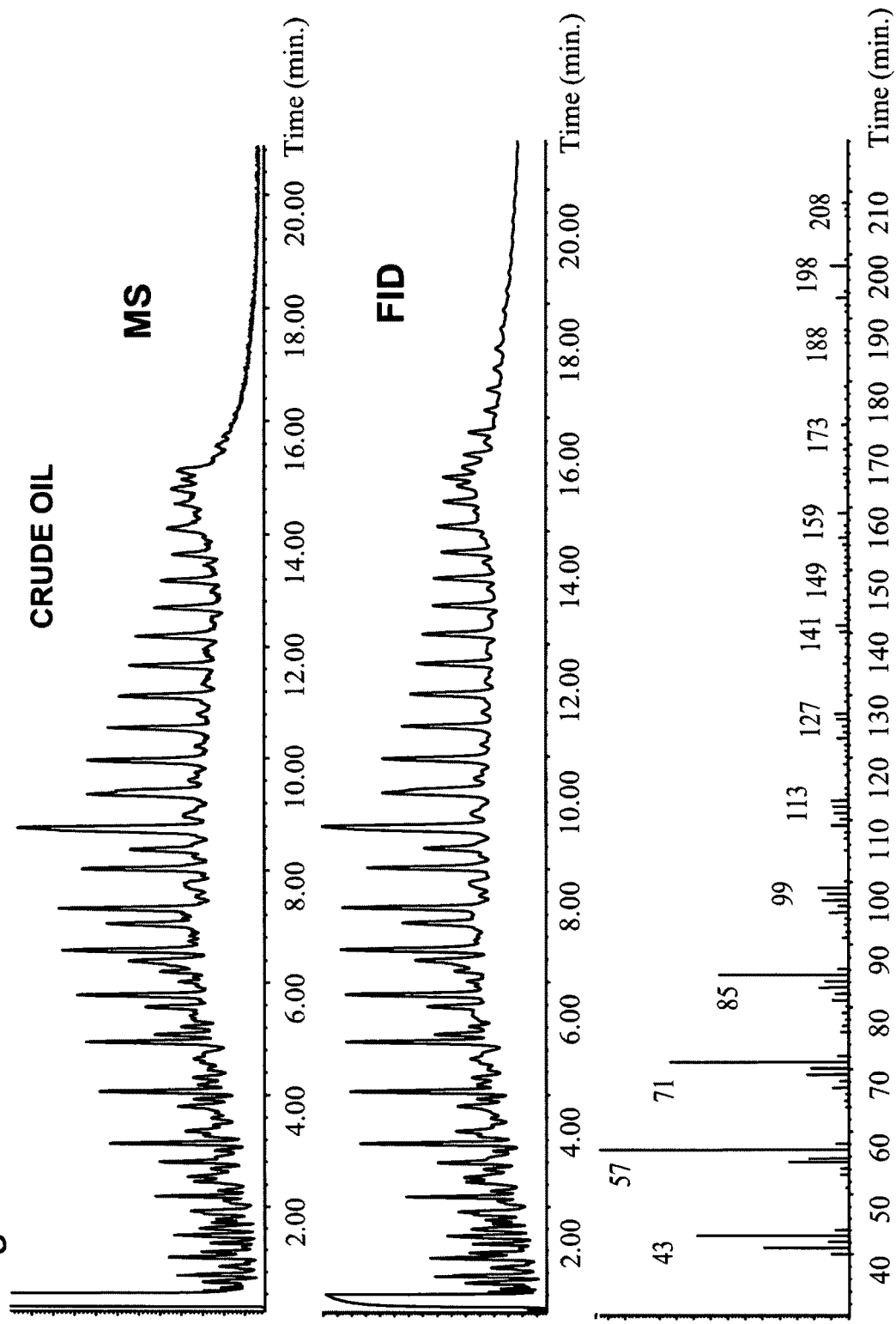
Figure 48:
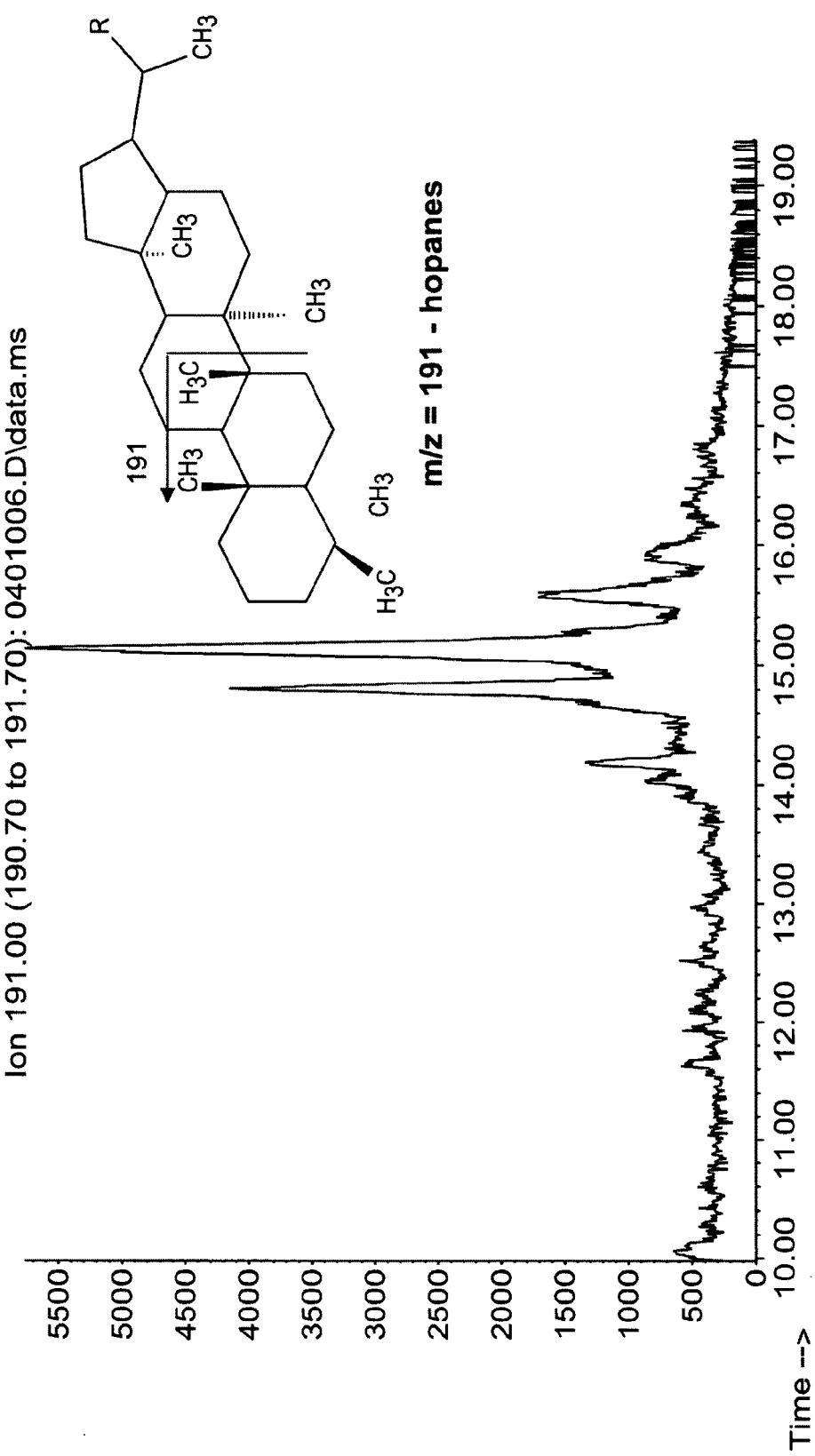
Figure 49:
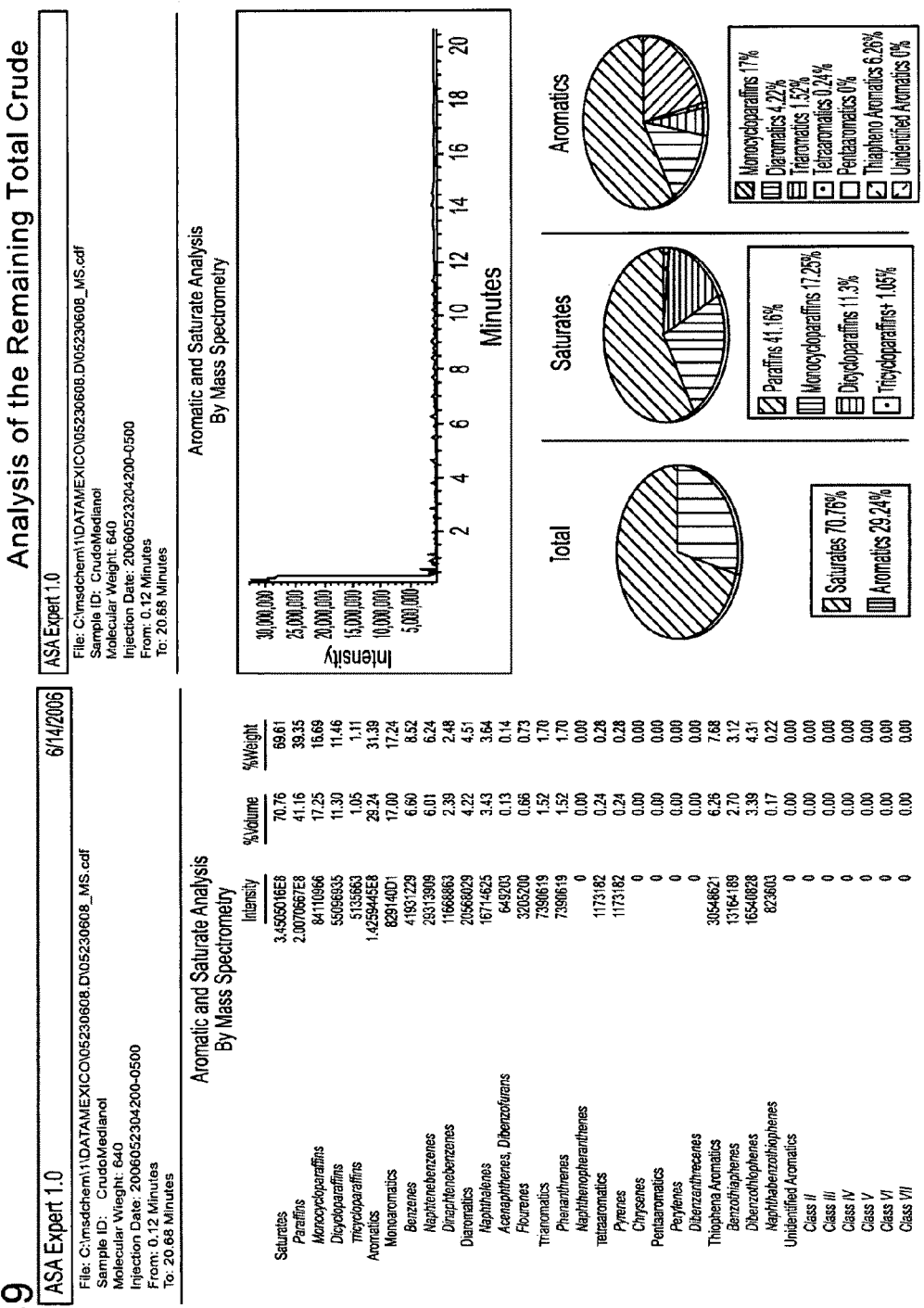
Figure 50:
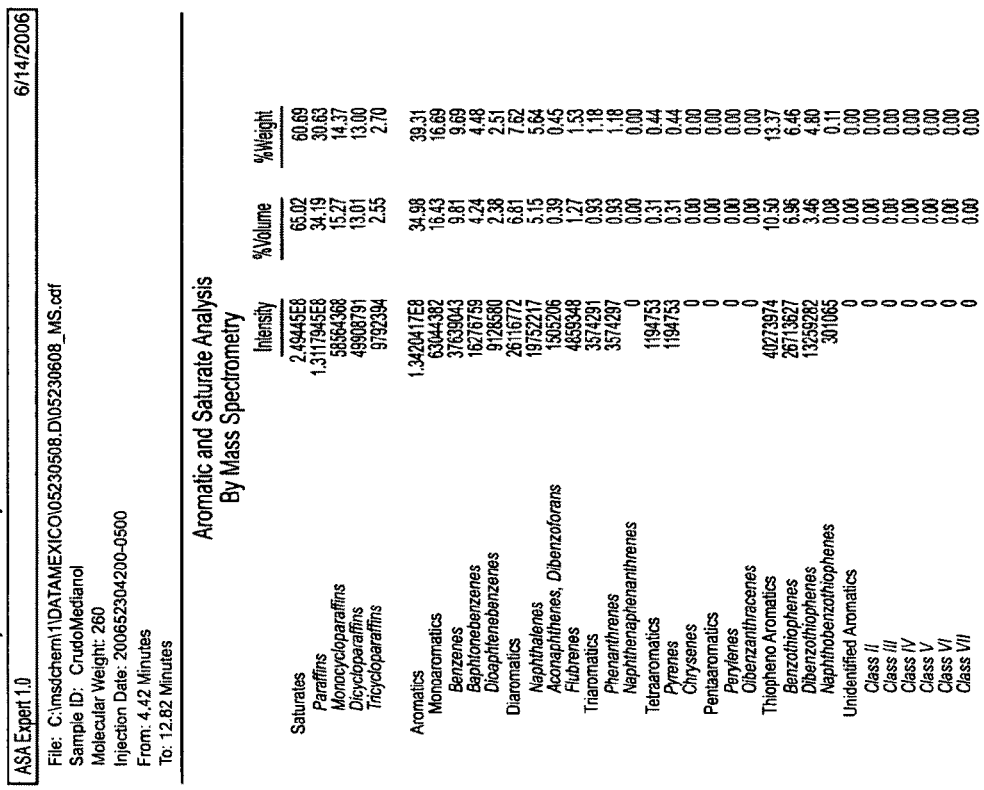
Figure 51:
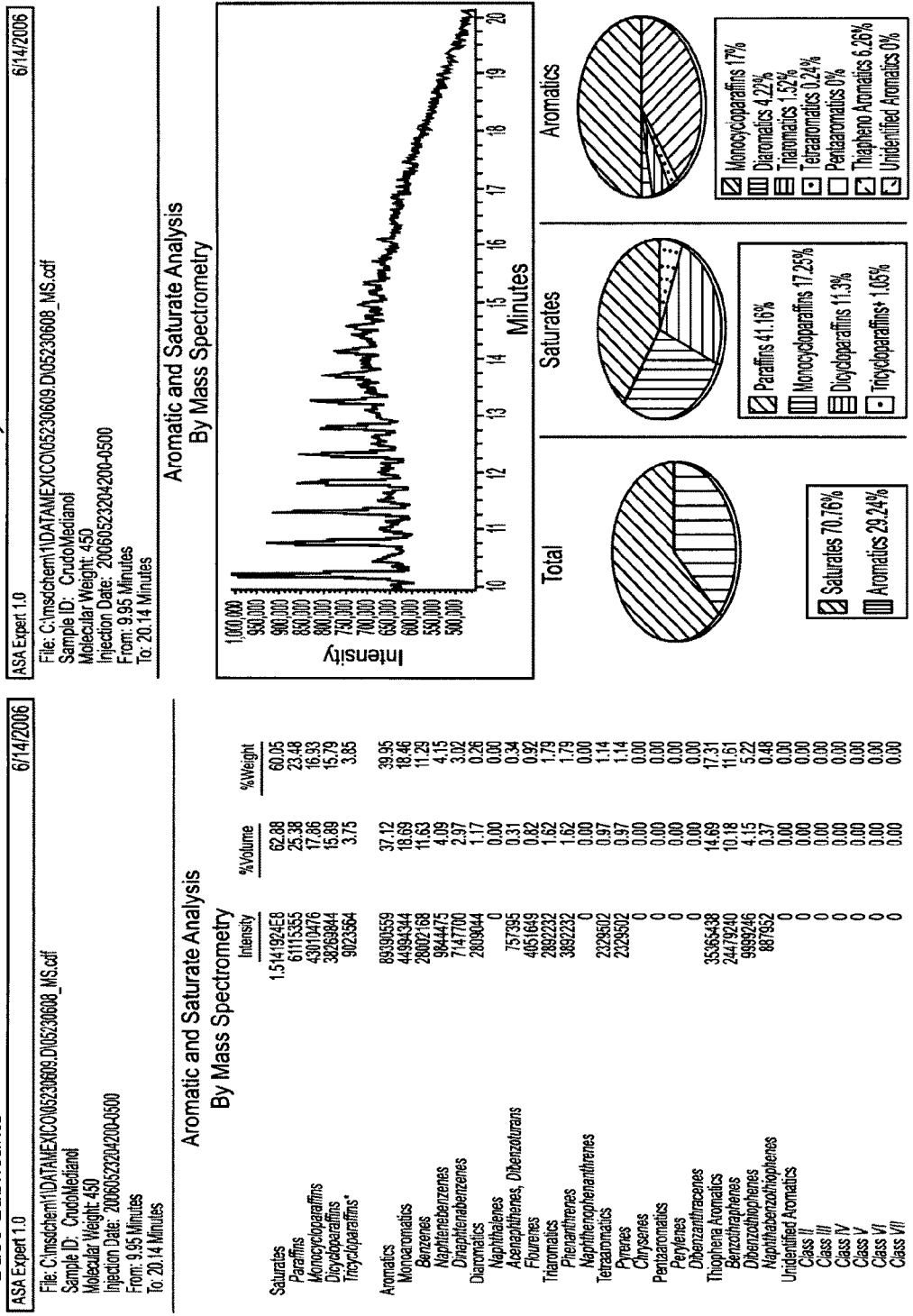

FIG. 7 shows a retention time standard for ASTM D 7169-2005. FIG. 8 shows a crude oil boiling point calibration curve. FIG. 9 shows the measured results of a reference material. FIG. 10 shows the measured results for a crude oil sample. FIG. 11 shows algorithms used for analyzing for each time slice the contributions of each ion characteristic of the hydrocarbon group of aromatics and saturates. Although FIG. 11 references algorithms disclosed in Robinson (Analytical Chemistry, Vo. 43, 11, 1971), these algorithms are exemplary only and other, more refined algorithms and multiple variant equations may be used to extract the various compositions of the various constituents of the sample being tested. These algorithms allow the superimposition of masses at various time intervals to extract the composition of each constituent. FIG. 12 shows a group type analysis of compounds that may be found within crude oil. FIG. 13 shows a retention time calibration standard, useable according to a method and system of an embodiment of the present invention. FIG. 14 shows a whole crude oil analysis, produced according to a method and system of an embodiment of the present invention. FIG. 15 shows experimental results of a measured fraction. FIG. 16 shows the signal overlapping from fractions, along with crude oil. FIG. 17 shows an analysis of Fraction #1. FIG. 18 shows an analysis of fraction #1 cut in whole crude. FIG. 19 shows the results of a sample of paraffinic light crude oil. FIG. 20 shows the results of a sample of paraffinic crude oil. FIG. 21 shows the results for samples of lube oil fractions. FIGS. 22 and 23 show a hydrocarbon type analysis from a whole crude sample. FIG. 24 shows a comparative study of middle hydrocarbon samples.

FIGS. 25-51 contain various data and other information produced using systems and methods of the present invention.

Example embodiments of the present invention have now been described in accordance with the above advantages. It will be appreciated that these examples are merely illustrative of the invention. Many variations and modifications will be apparent to those skilled in the art.

We claim:

1. A system for analyzing complex samples, the system comprising:
    a gas chromatograph including an injector and a column, wherein the injector is configured to insert a sample along with a flowing gas into the column;
    a flame ion detector (FID);
    a mass spectrometer; and
    a divider configured to divide constituents of the sample that are exiting the column for delivery to the flame ion detector and the mass spectrometer;
    wherein the divider is configured to prevent molecular discrimination within the constituents of the sample.

2. The system according to claim 1, wherein the system further comprises:
    a data processor for acquiring and processing data.

3. The system according to claim 2, wherein the data processor is configured to process the data by combining detection information from the flame ion detector and the mass spectrometer.

4. The system according to claim 2, wherein the data processor processes the data by combining detection information from the flame ion detector and the mass spectrometer via algorithms that allow the superimposition of masses at various intervals to extract a composition of the sample.

5. The system according to claim 1, wherein the injector is a temperature programmable injector.

6. The system according to claim 1, wherein the column is a wall coated capillary column.

7. The system according to claim 1, wherein the FID is in a simulated distillation mode.

8. The system according to claim 1, wherein the divider is configured to equally divide the constituents of the sample that are exiting the column.

9. The system according to claim 1, wherein the gas used in the gas chromatograph is Helium, and wherein the gas chromatograph is configured to maintain the gas at a constant flux of about 12 mL/minute.

10. The system according to claim 1, wherein the injector is configured to inject a sample of crude oil.

11. The system according to claim 1, wherein the injector is configured to inject a sample of a fraction of crude oil.

12. The system according to claim 1, wherein a controller controls a pressure of the sample to prevent molecular discrimination within the constituents of the sample.

13. The system according to claim 1, wherein the sample is heated to an appropriate temperature to prevent molecular discrimination.

14. The system according to claim 1, wherein the gas used in the gas chromatograph is hydrogen, and wherein the gas chromatograph is configured to maintain the gas at a constant flux of about 12 mL/minute.

15. The system of claim 1, wherein molecular discrimination is prevented by:
    a first portion of the constituents that is sent to the mass spectrometer and a second portion of the constituents that is sent to the flame ion detector being approximately equal; and
    an integrity of the constituents is preserved.

16. A method of analyzing a complex sample, the method including:
    injecting a sample with an injector into a column of a gas chromatograph along with a flowing gas;
    separating constituents of the sample within the column of the gas chromatograph;
    moving the constituents of the sample out of the column with the flowing gas;
    dividing the constituents of the sample that are exiting the column for delivery to a flame ion detector and a mass spectrometer;
    detecting characteristics of the constituents of the sample via the flame ion detector; and
    detecting characteristics of the constituents of the sample via the mass spectrometer;
    wherein dividing the constituents of the sample comprises preventing molecular discrimination within the constituents of the sample.

17. The method of claim 16, further comprising:
    acquiring and processing data from the detected characteristics obtained from the flame ion detector and the mass spectrometer.

18. The method of claim 17, wherein acquiring and processing the data includes:
    combining detection information from the flame ion detector and the mass spectrometer.

19. The method according to claim 17, wherein acquiring and processing data is performed via algorithms that allow the superimposition of masses at various intervals to extract a composition of the sample.

20. The method of claim 16, wherein the sample is injected with a temperature programmable injector.

21. The method of claim 16, wherein the sample is injected into wall coated capillary column.

22. The method of claim 16, wherein detecting characteristics of the constituents of the sample via the flame ion detector occurs in a simulated distillation mode.

23. The method of claim 16, wherein the divider approximately equally divides the constituents of the sample that are exiting the column.

24. The method of claim 16, wherein the flowing gas is helium, and the method further comprising:
    configuring the gas chromatograph to maintain the flowing gas at a constant flux of about 12 mL/minute.

25. The method of claim 16, wherein the sample is crude oil.

26. The method of claim 16, wherein the sample is a fraction of crude oil.

27. The method according to claim 16, wherein a controller controls a pressure of the sample to prevent molecular discrimination within the constituents of the sample.

28. The method according to claim 16, wherein the sample is heated to an appropriate temperature to prevent molecular discrimination.

29. The method of to claim 16, wherein the flowing gas is hydrogen, and the method further comprising:
   configuring the gas chromatograph to maintain the flowing gas at a constant flux of about 12 mL/minute.

30. The method of claim 16, wherein preventing molecular discrimination within the constituents of the sample comprises:
   having a first portion of the constituents that is sent to the mass spectrometer and a second portion of the constituents that is sent to the flame ion detector be approximately equal; and
   preserving an integrity of the constituents.

* * * * *